United States Patent
Kinnick et al.

(10) Patent No.: US 6,713,505 B2
(45) Date of Patent: Mar. 30, 2004

(54) SPLA$_2$ INHIBITORS

(75) Inventors: Michael Dean Kinnick, Indianapolis, IN (US); Ho-Shen Lin, Indianapolis, IN (US); Michael John Martinelli, Zionsville, IN (US); John Michael Morin, Brownsburg, IN (US); Michael Enrico Richett, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 10/297,282

(22) PCT Filed: Jun. 14, 2001

(86) PCT No.: PCT/US01/14855

§ 371 (c)(1),
(2), (4) Date: Dec. 3, 2002

(87) PCT Pub. No.: WO02/00641

PCT Pub. Date: Jan. 3, 2002

(65) Prior Publication Data

US 2003/0236232 A1 Dec. 25, 2003

Related U.S. Application Data

(60) Provisional application No. 60/214,566, filed on Jun. 28, 2000.

(51) Int. Cl.$^7$ .................. A61K 31/38; C07D 333/52
(52) U.S. Cl. ......................................... 514/443; 549/51
(58) Field of Search ........................... 514/443; 549/51

(56) References Cited

U.S. PATENT DOCUMENTS

| | | | |
|---|---|---|---|
| 6,084,120 A | * | 7/2000 | Alzeer et al. |
| 6,147,110 A | * | 11/2000 | Lesieur et al. |
| 6,162,930 A | * | 12/2000 | Pinney et al. |
| 6,225,288 B1 | * | 5/2001 | Han et al. |
| 6,262,055 B1 | * | 7/2001 | Young et al. |
| 6,302,837 B1 | * | 10/2001 | De Nanteuil et al. |
| 6,388,105 B1 | * | 5/2002 | Vuligonda et al. |
| 6,403,172 B1 | * | 6/2002 | Wingen et al. |
| 6,407,102 B1 | * | 6/2002 | Mahboobi et al. |
| 6,433,005 B1 | * | 8/2002 | McLaren et al. |

FOREIGN PATENT DOCUMENTS

| | | |
|---|---|---|
| EP | 1 016 660 | 7/2000 |
| GB | 2 024 220 | 1/1980 |

* cited by examiner

Primary Examiner—Deborah C Lambkin
(74) Attorney, Agent, or Firm—Francis O. Ginah

(57) ABSTRACT

A class of novel benzo(b)thiophene is disclosed together with the use of such compounds for inhibiting sPLA$_2$ mediated release of fatty acids for treatment of Inflammatory Diseases such as septic shock.

8 Claims, No Drawings

SPLA₂ INHIBITORS

This application claims benefit of provisional application No. 60/214,566 filed Jun. 28, 2000.

FIELD OF THE INVENTION

This invention relates to novel benzo(b)thiophene compounds useful for Inflammatory Diseases.

BACKGROUND OF THE INVENTION

The structure and physical properties of human non-pancreatic secretory phospholipase A₂ (hereinafter called, "sPLA₂") has been thoroughly described in two articles, namely, "Cloning and Recombinant Expression of Phospholipase A₂ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A₂" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds, which inhibit sPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

SUMMARY OF THE INVENTION

This invention provides novel benzo(b)thiophene compounds having potent and selective effectiveness as inhibitors of mammalian sPLA₂.

This invention is also the use of novel benzo(b)thiophene compounds useful in the treatment and/or prevention of Inflammatory Diseases.

This invention is also the use of novel benzo(b)thiophene compounds to inhibit mammalian sPLA₂ mediated release of fatty acids.

This invention is also a pharmaceutical composition containing any of the benzo(b)thiophene compounds of the invention.

I. Definitions

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The terms, "benzo(b)thiophene", "benzothiophene, or "benzo(b)thiophene" nucleus as used herein refer to a nucleus (having numbered positions) with the structural formula (X):

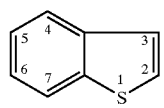

(X)

The benzo(b)thiophene compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3- dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

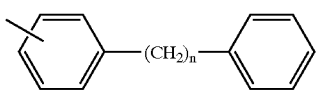
(a)

where n is a number from 1 to 8.

The term, "non-interfering substituent", refers to radicals suitable for substitution at positions 4,5,6 and/or 7 of the benzo(b)thiophene nucleus and on other nucleus substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —$(CH_2)_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where n is from 1 to 8 and R is $C_1$–$C_8$ alkyl.

The term, "organic substituent" refers to a monovalent radical consisting of carbon and hydrogen with or without oxygen, nitrogen, sulfur, halogen, or other elements. Illustrative organic substituents are $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the benzothiophene nucleus have been drawn to show the first line as a connecting bond only. Thus the group

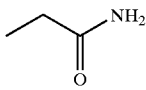

indicates the acetamide radical not propanamide unless otherwise indicated.

The term "substituted group" is an organic group substituted with one or more non-interfering substituents.

The term, "N-hydroxyfunctional amide group" is represented by the formula:

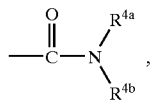

wherein, $R^{4a}$ is selected from the group consisting of OH, ($C_1$–$C_6$) alkoxy, and aryloxy; and wherein $R^{4b}$ is hydrogen or an organic substituent selected from the group consisting of $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substitued with halogen, —$CF_3$, —OH, $C_1$–$C_8$ alkyl, amino, carbonyl, and —CN.

The phrase, "N-hydroxyfunctional amide linker" refers to a divalent linking group symbolized as, —$(L_h)$—, which has the function of joining the 4 or 5—position of the benzo(b) thiophene nucleus to an N-hydroxyfunctional amide group in the general relationship:

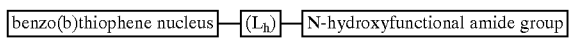

The words, "N-hydroxyfunctional amide linker length", refer to the number of atoms (excluding hydrogen) in the shortest chain of the linking group —$(L_h)$— that connects the 4 or 5—position of the benzo(b)thiophene nucleus with the N-hydroxyfunctional amide group. The presence of a carbocyclic ring in —$(L_h)$— counts as the number of atoms approximately equivalent to the calculated diameter of the carbocyclic ring. Thus, a benzene or cyclohexane ring in the acid linker counts as 2 atoms in calculating the length of —$(L_h)$—. Illustrative "N-hydroxyfunctional amide linker" groups are;

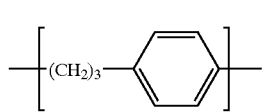
(a)

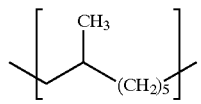
(b)

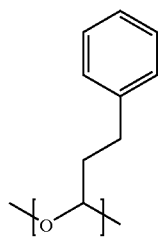
(c)

wherein, groups (a), (b) and (c) have acid linker lengths of 5, 7, and 2, respectively.

The term, "(acidic group)" means an organic group which when attached to a benzo(b)thiophene nucleus at the 4 or 5 position, through suitable linking atoms (hereinafter defined as the "acid linker"), acts as a proton donor capable of hydrogen bonding. Illustrative of an (acidic group) are the following:

-5-tetrazolyl,

—SO$_3$H,

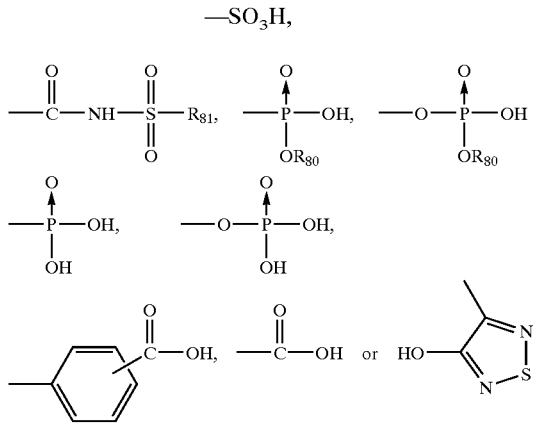

where n is 1 to 8, R$_{80}$ is a metal or C$_1$–C$_8$ and R$_{81}$ is an organic substituent or —CF$_3$.

The words, "acid linker" refer to a divalent linking group symbolized as, —(L$_a$)—, which has the function of joining the 4 or 5 position of the benzo(b)thiophene nucleus to an acidic group in the general relationship:

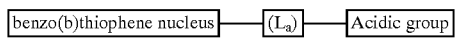

The words, "acid linker length", refer to the number of atoms (excluding hydrogen) in the shortest chain of the linking group —(L$_a$)— that connects the 4 or 5 position of the benzo(b)thiophene nucleus with the acidic group. The presence of a carbocyclic ring in —(L$_a$)— counts as the number of atoms approximately equivalent to the calculated diameter of the carbocyclic ring. Thus, a benzene or cyclohexane ring in the acid linker counts as 2 atoms in calculating the length of —(L$_a$)—. Illustrative acid linker groups are;

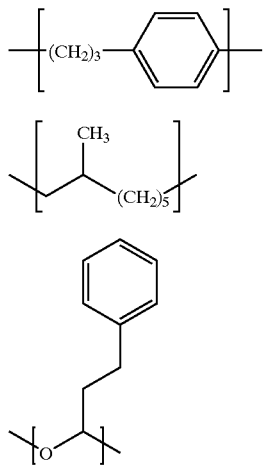

wherein, groups (a), (b), and (c) have acid linker lengths of 5, 7, and 2, respectively.

The term, "acylamino acid group" is represented by the formula:

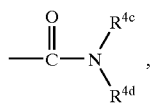

wherein R$^{4c}$ is selected from the group consisting of H, (C$_1$–C$_6$)alkyl, (C$_1$–C$_6$)alkoxy, heteroaryl and aryl, —CF$_3$; and wherein NR$^{4d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Contemplated within the definition of amino acid are l-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

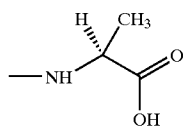

The words, "acylamino acid linker" refer to a divalent linking group symbolized as, —(L$_c$)—, which has the function of joining the 4 or 5—position of the benzo(b)thiophene nucleus to an acylamino acid group in the general relationship:

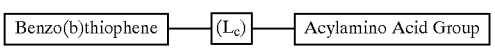

The words, "acylamino acid linker length", refer to the number of atoms (excluding hydrogen) in the shortest chain of the linking group —(L$_c$)— that connects the 4 or 5—position of the benzo(b)thiophene nucleus with the acylamino acid group. The presence of a carbocyclic ring in —(L$_c$)— counts as the number of atoms approximately equivalent to the calculated diameter of the carbocyclic ring. Thus, a benzene or cyclohexane ring in the acid linker counts as 2 atoms in calculating the length of —(L$_c$)—. Illustrative "acylamino acid linker groups" include:

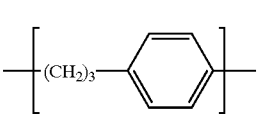

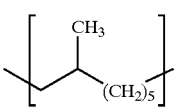

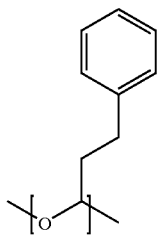

wherein, groups (a), (b) and (c) have acid linker lengths of 5, 7, and 2, respectively.

The term, "amine", includes primary, secondary and tertiary amines.

The terms, "mammal" and "mammalian" include human and domesticated quadrupeds.

The term, "alkylene chain of 1 or 2 carbon atoms" refers to the divalent radicals, —CH$_2$—CH$_2$— and —CH$_2$—.

The term, "group containing 1 to 10 non-hydrogen atoms" refers to relatively small groups which form substituents at the 2-position of the benzo(b)thiophene nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH=CH$_2$.

The term "oxime amide" means the radical, —C(=NOR)—C(O)NH$_2$.

The term "thio-oxime amide" means the radical —C(=NOR)—C(S)—NH$_2$.

The term "spiro[5.5]undecanyl" refers to the group represented by the formula;

II. The Benzo(b)thiophene Compounds of the Invention

The present invention provides novel classes of benzo(b)thiophene compounds useful as sPLA$_2$ inhibitors for the treatment of inflammation or inflammatory diseases. Classes of benzo(b)thiophene compounds of this invention include benzo(b)thiophene oxyacid derivatives, benzo(b)thiophene-3-oxime amide oxyacid derivatives, benzo(b)thiophene-3-acetamide oxyacid derivatives, benzo(b)thiophene-3-glyoxylamide N-hydroxyfunctional amide derivatives, benzo(b)thiophene-3-oxime amide N-hydroxyfunctional amide derivatives, benzo(b)thiophene-3-acetamide N-hydroxyfunctional amide derivatives, benzo(b)thiophene-3-glyoxylamide acylamino acid derivatives, benzo(b)thiophene-3-oxime amide acylamino acid derivatives, benzo(b)thiophene-3-acetamide acylamino acid derivatives.

The compounds of the invention have the general formula (I) or a pharmaceutically acceptable salt, solvate or prodrug thereof;

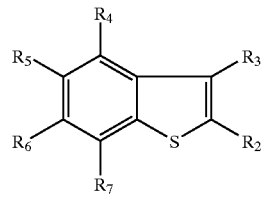

wherein

R$_2$ is hydrogen, or a group containing 1 to 10 non-hydrogen atoms plus any required hydrogen atoms;

R$_3$ is —(L$_3$)—Z, where —(L$_3$)— is a divalent linker group selected from a bond, or a divalent group selected from:

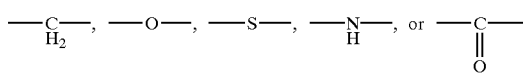

and Z is selected from an amide, thioamide, oxime amide, oxime thioamide, glyoxylamide, or acetamide group represented by the formulae,

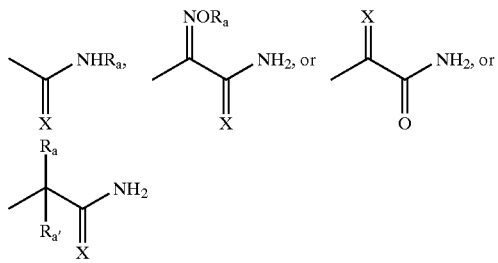

wherein X is oxygen or sulfur, R$_a$ and R$_{a'}$ are independently selected from hydrogen, C$_1$–C$_8$ alkyl, aryl, C$_1$–C$_8$ alkaryl, C$_1$–C$_8$ alkoxy, aralkyl and —CN;

R$_4$ is the group, hydrogen or —(La)-(acidic group) wherein —(L$_a$)—, is an acid linker having an acid linker length of 1 to 8;

or the group —(L$_h$)-(N-hydroxyfunctional amide group); wherein —(L$_h$)—, is an N-hydroxyfunctional amide linker having a N-hydroxyfunctional amide linker length of 1 to 8; and wherein a N-hydroxyfunctional amide group is represented by the formula:

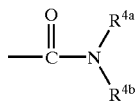

wherein R$^{4a}$ is selected from the group consisting of OH, (C$_1$–C$_6$)alkoxy, and aryloxy; and wherein R$^{4b}$ is hydrogen or an organic substituent selected from the group consisting of C$_1$–C$_8$ alkyl, aryl, C$_7$–C$_{14}$ aralkyl, C$_7$–C$_{14}$ alkaryl, C$_3$–C$_8$ cycloalkyl, C$_1$–C$_8$ alkoxyalkyl and these groups substitued with halogen, —CF$_3$, —OH, C$_1$–C$_8$ alkyl, amino, carbonyl, and —CN;

or R$_4$ is the group —(Lc)-(acylamino acid group) wherein the "acylamino acid group" is represented by the formula:

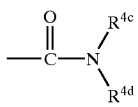

wherein $R^{4c}$ is selected from the group consisting of H, $(C_1-C_6)$alkyl, $(C_1-C_6)$alkoxy, heteroaryl and aryl, $-CF_3$; and wherein $NR^{4d}$ is an amino acid residue of either a natural or unnatural amino acid with the nitrogen atom being part of the amino group of the amino acid.

$R_5$ is selected from hydrogen, a non-interfering substituent, the group $-(L_h)$-(N-hydroxyfunctional amide group), or the group $-(L_c)$-acylamino acid group), or the group, $-(L_a)$-(acidic group); wherein $-(L_a)$—, is an acid linker having an acid linker length of 1 to 8; and provided that at least one of $R_4$ or $R_5$ is the group $-(L_h)$-(N-hydroxyfunctional amide group), or the group $-(L_c)$—acylamino acid group), or the group, $-(L_a)$-(acidic group).

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

Preferred Subgroups of Compounds of Formula (I)

Preferred $R_2$ Substituents $R_2$ is preferably selected from the group consisting of hydrogen, $C_1-C_4$ alkyl, $C_2-C_4$ alkenyl, $-O-(C_1-C_3$ alkyl), $-S-(C_1-C_3$ alkyl), $-C_3-C_4$ cycloalkyl $-CF_3$, halo, $-NO_2$, $-CN$, $-SO_3$. Particularly preferred $R_2$ groups are selected from hydrogen, methyl, ethyl, propyl, isopropyl, cyclopropyl, $-F$, $-CF_3$, $-Cl$, $-Br$, or $-O-CH_3$.

Preferred $R_3$ Substituents

A preferred subclass of compounds of formula (I) are those wherein X is oxygen.

Another preferred subclass of compounds of formula (I) are those wherein Z is an amide group.

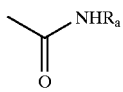

Another preferred subclass of compounds of formula (I) are those wherein Z is an oxime amide group.

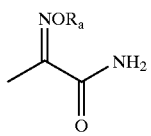

wherein $R_a$ selected from hydrogen, $C_1-C_8$alkyl, aryl, $C_1-C_8$ alkaryl, $C_1-C_8$ alkoxy, aralkyl and $-CN$.

Also preferred are compounds of formula (I) wherein Z is an acetamide group represented by the structure

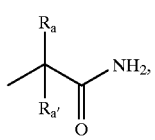

wherein $R_a$ and $R_{a'}$ are independently selected from hydrogen, $C_1-C_8$ alkyl, aryl, $C_1-C_8$ alkaryl, $C_1-C_8$ alkoxy, aralkyl and $-CN$. For the group $R_3$ it is most preferred that the linking group $-(L_3)$— be a bond.

Preferred $R_4$ Substituents

A preferred subclass of compounds of formula I are those wherein $R_4$ is a substituent selected from hydrogen, a non-interfering substituent, or the group, $-(L_a)$-(acidic group); wherein $-(L_a)$— is an acid linker; provided the acid linker group, $-(L_a)$— for $R_4$ is selected from the group consisting of;

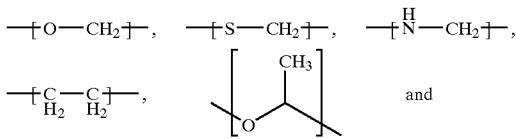

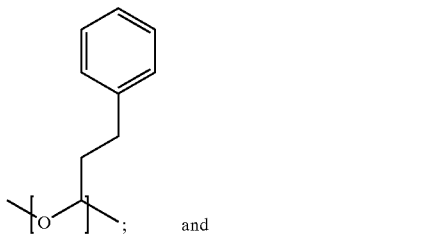

provided, that at least one of $R_4$ and $R_5$ must be the group, $-(L_a)$-(acidic group) or the group $-(L_h)$-(N-hydroxyfunctional amide group) or the group $-(Lc)$-(acylamino acid group), and wherein the (acidic group) on the group $-(L_a)$-(acidic group) of $R_4$ or $R_5$ is selected from $-CO_2H$, $CO_2Na$, $CO_2R_a$, $-SO_3H$, or $-P(O)(OH)_2$;

Another preferred subclass of compounds of formula I are those wherein $R_4$ is the group $-(Lc)$-(acylamino acid group)-, wherein $-(Lc)$— is an acylamino acid linker with an acylamino acid linker length of 2 or 3, and the "acylamino acid group" is represented by the formula:

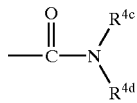

wherein $R^{4c}$ is selected from the group consisting of H, $(C_1-C_6)$alkyl, $(C_1-C_6)$alkoxy, heteroaryl and aryl, $-CF_3$; and wherein $NR^{4d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Another preferred subclass of compounds of formula (I) are those wherein $R_4$ is a substituent having an N-hydroxyfunctional amide linker with an N-hydroxyfunctional amide linker length of 2 or 3 and the N-hydroxyfunctional amide linker group, $-(L_h)$—, for $R_4$ is selected from a group represented by the formula;

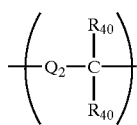

where $Q_2$ is selected from the group $-(CH_2)$—, $-O-$, $-NH-$, $-C(O)-$, and $-S-$, and each $R_{40}$ is independently selected from hydrogen, $C_1$–$C_8$ alkyl, aryl, $C_1$–$C_8$ alkaryl, $C_1$–$C_8$ alkoxy, aralkyl, and halo.

Most preferred subclasses of compound of formula (I) are compounds where the acid linker —($L_a$)—, or the N-hydroxyfunctional amide linker, —($L_h$)—, or the acylamino acid linker —($L_c$)—, for $R_4$ is independently selected from the specific groups;

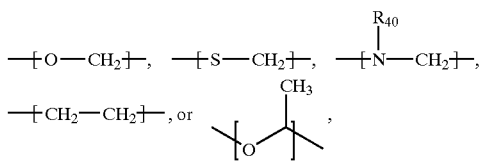

wherein $R_{40}$ is hydrogen or $C_1$–$C_8$ alkyl.

Preferred as the N-hydroxyfunctional amide group in the group $R_4$ is the group:

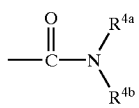

wherein $R^{4a}$ is selected from the group consisting of OH, ($C_1$–$C_6$)alkoxy and aryloxy; and wherein $R^{4b}$ is an organic substituent selected from the group consisting of H, $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substituted with halogen, —$CF_3$, —OH, $C_1$–$C_8$ alkyl, amino, carbonyl, and —CN. A more preferred $R^{4a}$ group is selected from the group consisting of —OH, —$OCH_3$ and —$OC_2H_5$ while a more preferred $R^{4b}$ is selected from the group consisting of H, $C_1$–$C_8$ alkyl, aryl, $C_7$–$C_{14}$ aralkyl, $C_7$–$C_{14}$ alkaryl, $C_3$–$C_8$ cycloalkyl. A most preferred $R^{4b}$ is a group selected from H, $CH_3$, $C_2H_5$ and $C_3H_7$.

A salt or a prodrug derivative of the (N-hydroxyfunctional amide group) is also a suitable substituent.

Preferred $R_5$ Substituents

Preferred acid linker, —($L_a$)—, for $R_5$ is selected from the group consisting of;

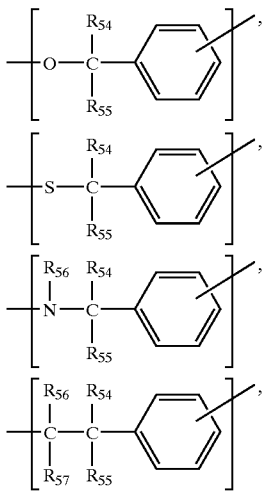

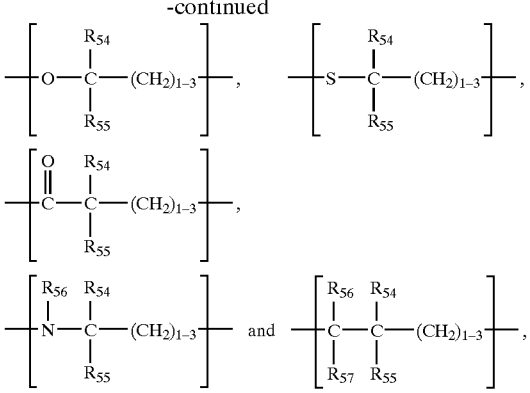

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo. Preferred (acidic group) for $R_5$ is selected from the group consisting of —$CO_2H$, —$SO_3H$ and —P(O)(OH)$_2$. Most preferred for $R_5$ is the group hydrogen or a non-interfering substituent.

Preferred $R_6$ and $R_7$ Substituents

Another preferred subclass of compounds of formula (I) are those wherein for $R_6$ and $R_7$ the non-interfering substituent is independently methyl, ethyl, propyl, isopropyl, thiomethyl, —O-methyl, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where n is from 1 to 8.

Most preferred as non-interfering substituents are methyl, ethyl, propyl, and isopropyl.

Most preferred compounds of the invention are those having the general formula (II) or (II') or (III) or a pharmaceutically acceptable salt, solvate or prodrug derivative thereof;

(II)

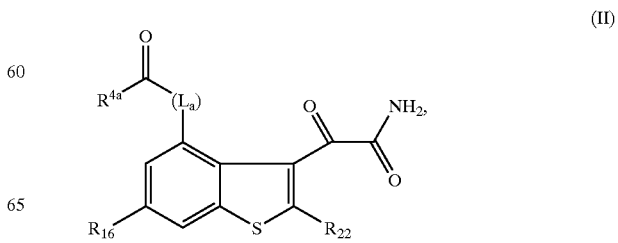

-continued

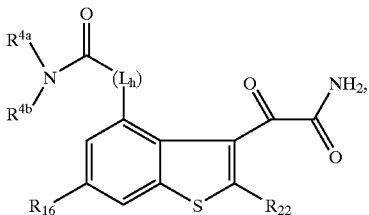
(II')

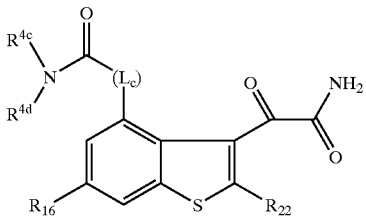
(III)

wherein;

R$_{22}$ is selected from hydrogen, methyl, ethyl, propyl, isopropyl, cyclopropyl, —F, —CF$_3$, —Cl, —Br, or —O—CH$_3$;

wherein R$^{4c}$ is independently selected from the group consisting of H, OH, (C$_1$–C$_6$)alkyl, (C$_1$–C$_6$)alkoxy, heteroaryl and aryl; and wherein R$^{4d}$ is independently selected from the group consisting of H, C$_1$–C$_8$ alkyl, aryl, C$_7$–C$_{14}$ aralkyl, C$_7$–C$_{14}$ alkaryl, C$_3$–C$_8$ cycloalkyl or combine with the nitrogen atom to form an "amino acid residue". A more preferred R$^{4c}$ group is the group H, OH, or OCH$_3$. A more preferred R$^{4d}$ group is the group H, or (C$_1$–C$_6$)alkyl. A more preferred —(L$_a$)—, —(L$_c$)—, or —(L$_h$)— is independently a divalent group selected from;

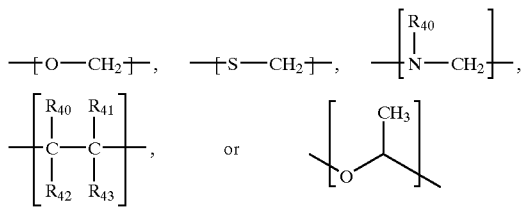

where R$_{40}$, R$_{41}$, R$_{42}$, and R$_{43}$ are each independently selected from hydrogen or C$_1$–C$_8$ alkyl.

R$_{16}$ is selected from hydrogen, C$_1$–C$_8$ alkyl, C$_1$–C$_8$ alkoxy, C$_1$–C$_8$ alkylthio, C$_1$–C$_8$ haloalkyl, C$_1$–C$_8$ hydroxyalkyl, and halo.

The Acylamino Acid Benzo(b)thiophene Compounds of the Invention

The benzo(b)thiophene acylamino acid compounds of the invention have the general formula (I) or a pharmaceutically acceptable salt, solvate or prodrug thereof;

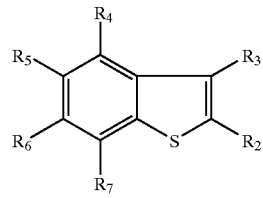
(I)

wherein;

R$_2$ is as described previously;

R$_3$ is —(L$_3$)—Z, where —(L$_3$)— is a divalent linker group selected from a bond or a divalent group selected from:

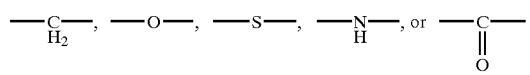

and Z is selected from an amide, thioamide or glyoxylamide, acetamide or thioacetamide radical (group} represented by the formulae,

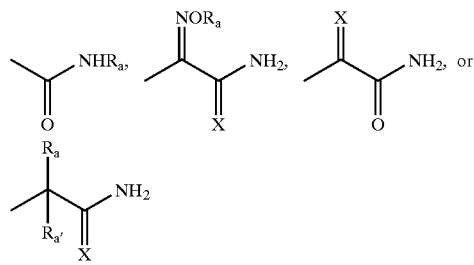

wherein X is oxygen or sulfur, R$_a$ and R$_{a'}$ are independently selected from hydrogen, C$_1$–C$_8$ alkyl, aryl, C$_1$–C$_8$ alkaryl;

R$_4$ is the group, —(L$_c$)-(acylamino acid group); wherein —(L$_c$)—, is an acylamino acid linker having an acylamino acid linker length of 1 to 8;

R$_5$ is selected from hydrogen, a non-interfering substituent, or the group, —(L$_a$)-(acidic group); wherein —(L$_a$)—, is an acid linker having an acid linker length of 1 to 8.

R$_6$ and R$_7$ are selected from hydrogen, non-interfering substituent, carbocyclic radical, carbocyclic radical substituted with non-interfering substituent(s), heterocyclic radicals, and heterocyclic radical substituted with non-interfering substituent (s).

Preferred R$_4$ Substituents

A preferred subclass of compounds of formula (I) are those wherein R$_4$ is a substituent having an acylamino acid linker with an acylamino acid linker length of 2 or 3 and the acylamino acid linker group, —(L$_c$)—, for R$_4$ is selected from a group represented by the formula;

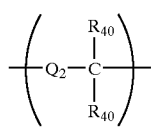

where Q$_2$ is selected from the group —(CH$_2$)—, —O—, —NH—, —C(O)—, and —S—, and each R$_{40}$ is independently selected from hydrogen, C$_1$–C$_8$ alkyl, aryl, C$_1$–C$_8$ alkaryl, C$_1$–C$_8$ alkoxy, aralkyl, and halo. Most preferred are compounds where the acylamino acid linker, —(L$_c$)—, for R$_4$ is selected from the specific groups;

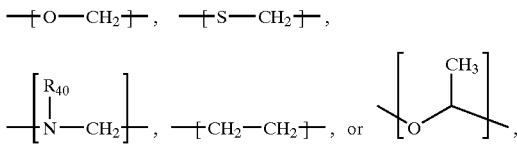

where R$_{40}$ is hydrogen or C$_1$–C$_8$ alkyl.

Preferred as the (acylamino acid group) in the group R$_4$ is the group:

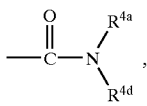

wherein R$^{4c}$ is selected from the group consisting of H, (C$_1$–C$_6$)alkyl, (C$_1$–C$_6$)alkoxy, heteroaryl and aryl; and wherein NR$^{4d}$ is an amino acid residue of either a natural or unnatural amino acid with the nitrogen atom being part of the amino group of the amino acid. A most preferred R$^{4c}$ group is the group hydrogen (H). A preferred source of amino acid residue is the amino acid group selected from the group comprising isoleucine, valine, phenylalanine, aspartic acid, leucine, glycine and isomers and derivatives thereof. A salt or a prodrug derivative of the (acylamino acid group) is also a suitable substituent.

Particularly preferred are R$^{4d}$ groups that combine with the nitrogen atom to represent amino acid residues from the amino acid groups selected from: glycine, glycine methyl ester, L-alaninie, L-alanine methylester, L-leucine, L-leucine methyl ester, L-aspartic acid, L-aspartic acid dimethylester, L-phenyl alanine, L-phenylalanine methyl ester, malonic acid, malonic acid dimethylester, L-valine, L-valine methyl ester, L-isoleucine, L-isoleucine methyl ester, or salt, and derivatives thereof.

Preferred acylamino acid compounds of the invention are those having the general formula (III), or a pharmaceutically acceptable salt, solvate or prodrug derivative thereof;

(III)

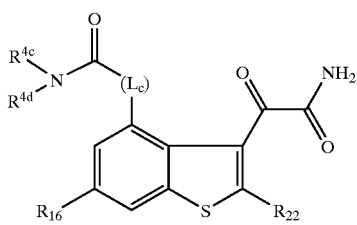

wherein;

R$_{22}$ is selected from hydrogen, methyl, ethyl, propyl, isopropyl, cyclopropyl, —F, —CF$_3$, —Cl, —Br, or —O—CH$_3$;

wherein R$^{4c}$ is selected from the group consisting of H, (C$_1$–C$_6$)alkyl, (C$_1$–C$_6$)alkoxy, heteroaryl and aryl; and wherein NR$^{4d}$ is an amino acid residue of either a natural or unnatural amino acid with the nitrogen atom being part of the amino group of the amino acid. A preferred R$^{4c}$ group is the group hydrogen (H); and —(Lc)— is a divalent group selected from;

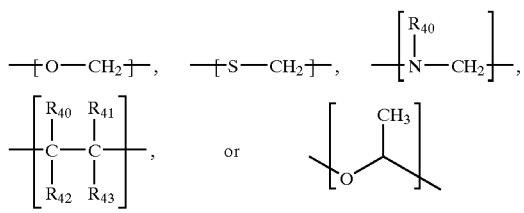

where R$_{40}$, R$_{41}$, R$_{42}$, and R$_{43}$ are each independently selected from hydrogen or C$_1$–C$_8$ alkyl.

R$_{16}$ is selected from hydrogen, C$_1$–C$_8$ alkyl, C$_1$–C$_8$ alkoxy, C$_1$–C$_8$ alkylthio, C$_1$–C$_8$ haloalkyl, C$_1$–C$_8$ hydroxyalkyl, and halo.

The benzo(b)thiophene-3-acetamide sPLA$_2$ Inhibitor Compounds

The benzo(b)thiophene-3-acetamide sPLA$_2$ inhibitor compounds of the present invention are represented by compounds of formula (IIIb), and pharmaceutically acceptable salts and prodrug derivatives thereof, (IIIb)

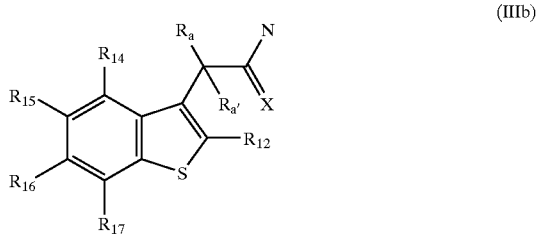

wherein;

X is oxygen or sulfur;

R$_{12}$ is halo, C$_1$–C$_2$ alkylthio, C$_1$–C$_4$ alkyls, C$_1$–C$_{12}$ alkylaryl or C$_1$–C$_2$ alkoxy;

R$_a$ and R$_{a'}$ are independently selected from hydrogen, C$_1$–C$_8$ alkyl, aryl, C$_1$–C$_8$ alkaryl;

R$_{14}$ is the group, —(L$_h$)-(N-hydroxyfunctional amide group); wherein —(L$_h$)—, is an N-hydroxyfunctional amide linker having an N-hydroxyfunctional amide linker length of 1 to 8; and wherein a N-hydroxyfunctional amide is represented by the formula:

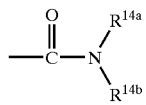

wherein R$^{14a}$ is selected from the group consisting of OH, (C$_1$–C$_6$)alkoxy, and aryloxy; and wherein R$^{14b}$ is hydrogen or an organic substituent selected from the group consisting of C$_1$–C$_8$ alkyl, aryl, C$_7$–C$_{14}$ aralkyl, C$_7$–C$_{14}$ alkaryl, C$_3$–C$_8$ cycloalkyl, C$_1$–C$_8$ alkoxyalkyl and these groups substituted with halogen, —CF$_3$, —OH, C$_1$–C$_8$ alkyl, amino, carbonyl, and —CN; or R$_{14}$ is the group hydrogen, —(L$_a$)-(acidic group); wherein —(L$_a$)—, is an acid linker having an acid linker length of 1 to 8; or the group —(Lc)-acylamino acid group), wherein —(Lc)—, is an acylamino acid linker having an acylamino acid linker length of 1 to 8;

R$_{15}$, R$_{16}$, and R$_{17}$ are each independently hydrogen, C$_1$–C$_{10}$ alkyl, C$_1$–C$_{10}$ alkenyl, C$_1$–C$_{10}$ alkynyl, C$_3$–C$_8$ cycloalkyl, aryl, aralkyl, or any two adjacent hydrocarbyl groups in the set $R_{15}$, $R_{16}$, and $R_{17}$, combine with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, $C_1$–$C_{10}$ alkylthio, arylthio, thioacetal, —C(O)O($C_1$–$C_{10}$ alkyl), hydrazide, hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5- to 8-membered heterocyclic ring; or a group having the formula;

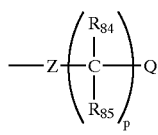

where, $R_{84}$ and $R_{85}$ are each independently selected from hydrogen, $C_1$–$C_{10}$ alkyl, hydroxy, or $R_{84}$ and $R_{85}$ taken together are =O;

p is 1 to 5,

Z is a bond, —O—, —N($C_1$–$C_{10}$ alkyl)-, —NH—, or —S—; and

Q is —CON($R_{82}$R$_{83}$), -5-tetrazolyl, —SO$_3$H,

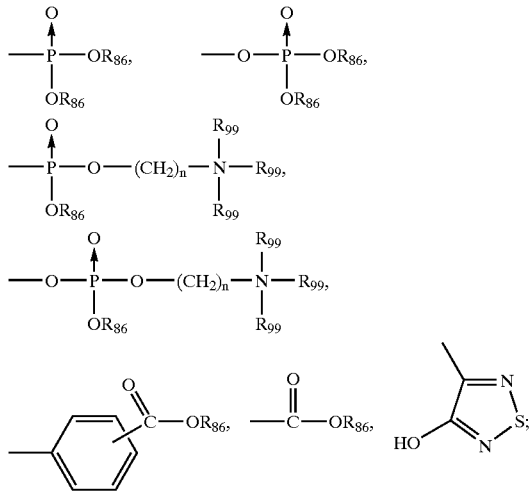

where n is 1 to 8, $R_{86}$ is independently selected from hydrogen, a metal, or $C_1$–$C_{10}$ alkyl, and $R_{99}$ is selected from hydrogen or $C_1$–$C_{10}$ alkyl.

The Benzo(b)thiophene-3-amide Compounds

Compounds of formula (IV) or a pharmaceutically acceptable salt, solvate or prodrug represent benzo(b)thiophene-3-amide compounds of the invention thereof;

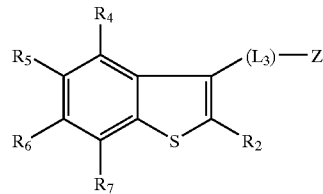

wherein;

$R_2$ is hydrogen, or a group containing 1 to 4 non-hydrogen atoms plus any required hydrogen atoms;

—(L$_3$)—Z, is the group where —(L$_3$)— is a divalent linker group selected from a bond or a divalent group selected from:

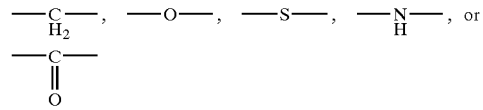

and Z is selected from an amide or thioamide radical or group represented by the formulae,

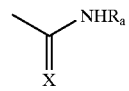

wherein, X is oxygen or sulfur; and $R_a$ is selected from hydrogen, $C_1$–$C_8$ alkyl, aryl, $C_1$–$C_8$ alkaryl;

$R_4$ is the group, the group, —(L$_a$)-(acidic group); wherein —(L$_a$)—, is an acid linker having an acid linker length of 1 to 8, or —(L$_h$)-(N-hydroxyfunctional amide group); wherein —(L$_h$)—, is an N-hydroxyfunctional amide linker having an N-hydroxyfunctional amide linker length of 1 to 8; or the group —(L$_c$)-(acylamino acid group); wherein —(L$_c$)— is an acylamino acid linker having an acylamino acid linker length of 1 to 8.

$R_5$ is selected from hydrogen, a non-interfering substituent, or the group, —(L$_a$)-(acidic group); wherein —(L$_a$)—, is an acid linker having an acid linker length of 1 to 8.

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

The Benzo(b)thiophene-3-Glyoxylamide Compounds

Compounds of formula (IV) or a pharmaceutically acceptable salt, solvate or prodrug represent benzo(b)thiophene-3-glyoxylamide compounds of the invention thereof;

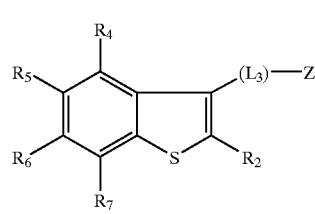

wherein;

$R_2$ is hydrogen, or a group containing 1 to 4 non-hydrogen atoms plus any required hydrogen atoms;

—(L₃)—Z, is the group where —(L₃)— is a divalent linker group selected from a bond or a divalent group selected from:

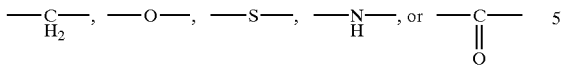

and Z is selected from glyoxylamide group represented by the formulae,

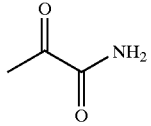

wherein $R_4$ is the group, —(L$_a$)-(acidic group); wherein —(L$_a$)—, is an acid linker having an acid linker length of 1 to 8, or —(L$_h$)-(N-hydroxyfunctional amide group); wherein —(L$_h$)—, is an N-hydroxyfunctional amide linker having an N-hydroxyfunctional amide linker length of 1 to 8; or the group —(L$_c$)-(acylamino acid group); wherein —L$_c$— is an acylamino acid linker having an acylamino acid linker length of 1 to 8.

$R_5$ is selected from hydrogen, a non-interfering substituent, or the group, —(L$_a$)-(acidic group); wherein —(L$_a$)—, is an acid linker having an acid linker length of 1 to 8; and provided that when $R_4$ is —(L$_a$)-(acidic group); or —(L$_h$)-(N-hydroxyfunctional amide group); or —(L$_c$)—acylamino acid group), $R_4$ cannot be —(L$_a$)-(acidic group); or —(L$_h$)-(N-hydroxyfunctional amide group); or —(L$_c$)-(acylamino acid group).

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

The Benzo(b)thiophene-3-oxime Amide Compounds

Compounds of formula (V) or a pharmaceutically acceptable salt, solvate or prodrug represent benzo(b)thiophene-3-oxime amide compounds of the invention thereof;

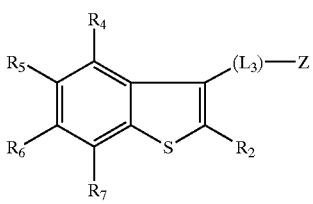

(V)

wherein;

$R_2$ is hydrogen, or a group containing 1 to 4 non-hydrogen atoms plus any required hydrogen atoms;

—(L₃)—Z, is the group where —(L₃)— is a divalent linker group selected from a bond or a divalent group selected from:

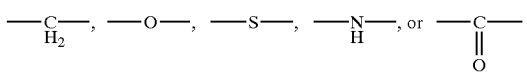

and Z is selected from an oxime amide group represented by the formulae,

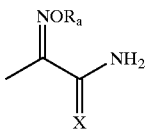

wherein, X is oxygen or sulfur; and $R_a$ is selected from hydrogen, $C_1$–$C_8$ alkyl, aryl, $C_1$–$C_8$ alkaryl, $C_1$–$C_8$ alkoxy, aralkyl and —CN;

$R_4$ is the group, the group, —(L$_a$)-(acidic group); wherein —(L$_a$)—, is an acid linker having an acid linker length of 1 to 8, or —(L$_h$)-(N-hydroxyfunctional amide group); wherein —(L$_h$)—, is an N-hydroxyfunctional amide linker having an N-hydroxyfunctional amide linker length of 1 to 8; or the group —(L$_c$)-(acylamino acid group); wherein —L$_c$— is an acylamino acid linker having an acylamino acid linker length of 1 to 8.

$R_5$ is selected from hydrogen, a non-interfering substituent, or the group, —(L$_a$)-(acidic group); wherein —(L$_a$)—, is an acid linker having an acid linker length of 1 to 8.

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

Preferred specific compounds (and all pharmaceutically acceptable salts, solvates and prodrug derivatives thereof) which are illustrative of the compounds of the invention are as follow:

[[3-(2-Amino-1,2-dioxoethyl)-2-methylbenzo(b)thiophen-4-yl]oxy]acetic acid;

d1-2-[[3-(2-Amino-1,2-dioxoethyl)-2-methylbenzo(b)thiophen-4-yl]oxy]propanoic acid;

[[3-(2-Amino-1,2-dioxoethyl)-2-ethylbenzo(b)thiophen-4-yl]oxy]acetic acid;

[[3-(2-amino-1,2-dioxoethyl)-2-propylbenzo(b)thiophen-4-yl]oxy]acetic acid;

[[3-(2-Amino-1,2-dioxoethyl)-2-cyclopropylbenzo(b)thiophen-4-yl]oxy]acetic acid;

4-[[3-(2-Amino-1,2-dioxoethyl)-2-ethylbenzo(b)thiophen-5-yl]oxy]butanoic acid;

2-[[3-(Aminooxoacetyl)-2-ethylbenzo(b)thiophen-4-yl]oxy]-N-(hydroxy)acetamide;

2-[[3-(Aminooxoacetyl)-2-ethybenzo(b)thiophen-4-yl]oxy]-N-(methyloxy)acetamide;

2-[[3-(Aminooxoacetyl)-2-ethylbenzo(b)thiophen-4-yl]oxy]-N-(methyl)-N-(methyloxy)acetamide;

2-[[3-(Aminooxoacetyl)-2-ethylbenzo(b)thiophen-4-yl]oxy]-N-(hydroxy)-N-(methyl)acetamide;

2-[[3-(Aminooxoacetyl)-2-ethylbenzo(b)thiophen-4-yl]oxy]-N-(ethyloxy)acetamide;

2-[[3-(Aminooxoacetyl)-2-ethylbenzo(b)thiophen-4-yl]oxy]-N-(2-propenyloxy)acetamide;

2-[[3-(Aminooxoacetyl)-2-ethylbenzo(b)thiophen-4-yl]oxy]-N-(hydroxy)-N-(2-propyl)acetamide;

2-[[3-(Aminooxoacetyl)-2-ethylbenzo(b)thiophen-4-yl]oxy]-N-(tert-butyloxy)acetamide;

2-[[3-(Aminooxoacetyl)-2-ethylbenzo(b)thiophen-4-yl]oxy]-N-[2-(methyl)propyloxy]acetamide;

2-[[3-(Aminooxoacetyl)-2-ethylbenzo(b)thiophen-4-yl]oxy]-N-(phenylmethyloxy)acetamide;

2-[[3-(Aminooxoacetyl)-2-ethylbenzo(b)thiophen-4-yl]oxy]-N-(methyl)-N-(phenylmethyloxy)acetamide;

2-[[3-(Aminooxoacetyl)-2-ethylbenzo(b)thiophen-4-yl]oxy]-N-(phenyloxy)acetamide;

2-[[3-(Aminooxoacetyl)-2-ethylbenzo(b)thiophen-4-yl]oxy]-N-(methyl)-N-(phenyloxy)acetamide;
2-[[3-(Aminooxoacetyl)-2-ethylbenzo(b)thiophen-4-yl]oxy]-N-(cyclohexyl)-N-(hydroxy)acetamide;
2-[[3-(2-Amino-2-oxoethyl)-2-ethylbenzo(b)thiophen-4-yl]oxy]-N-(hydroxy)acetamide;
N-[2-[[3-(Aminooxoacetyl)-2-ethylbenzo(b)thiophen-4-yl]oxy]acetyl]glycine;
N-[2-[[3-(Aminooxoacetyl)-2-ethylbenzo(b)thiophen-4-yl]oxy]acetyl]glycine methyl ester;
N-[2-[[3-(Aminooxoacetyl)-2-ethylbenzo(b)thiophen-4-yl]oxy]acetyl]-L-alanine;
N-[2-[[3-(Aminooxoacetyl)-2-ethylbenzo(b)thiophen-4-yl]oxy]acetyl]-L-alanine methyl ester;
N-[2-[[3-(Aminooxoacetyl)-2-ethylbenzo(b)thiophen-4-yl]oxy]acetyl]-L-leucine;
N-[2-[[3-(Aminooxoacetyl)-2-ethylbenzo(b)thiophen-4-yl]oxy]acetyl]-L-leucine methyl ester;
N-[2-[[3-(Aminooxoacetyl)-2-ethylbenzo(b)thiophen-4-yl]oxy]acetyl]-L-aspartic acid;
N-[2-[[3-(Aminooxoacetyl)-2-ethylbenzo(b)thiophen-4-yl]oxy]acetyl]-L-aspartic acid dimethyl ester;
N-[2-[[3-(Aminooxoacetyl)-2-ethylbenzo(b)thiophen-4-yl]oxy]acetyl]-L-phenylalanine;
N-[2-[[3-(Aminooxoacetyl)-2-ethylbenzo(b)thiophen-4-yl]oxy]acetyl]-L-phenylalanine methyl ester;
[2-[[3-(Aminooxoacetyl)-2-ethylbenzo(b)thiophen-4-yl]oxy]acetamido]malonic acid;
[2-[[3-(Aminooxoacetyl)-2-ethylbenzo(b)thiophen-4-yl]oxy]acetamido]malonic acid dimethyl ester
N-[2-[[3-(Aminooxoacetyl)-2-ethylbenzo(b)thiophen-4-yl]oxy]acetyl]-L-valine;
N-[2-[[3-(Aminooxoacetyl)-2-ethylbenzo(b)thiophen-4-yl]oxy]acetyl]-L-valine methyl ester;
N-[2-[[3-(Aminooxoacetyl)-2-ethylbenzo(b)thiophen-4-yl]oxy]acetyl]-L-isoleucine; and
N-[2-[[3-(Aminooxoacetyl)-2-ethylbenzo(b)thiophen-4-yl]oxy]acetyl]-L-isoleucine methyl ester.

The salts of the above benzo(b)thiophene compounds represented by formulae (I), (II), (II'), (III), (IIIb), and (IV) are an additional aspect of the invention. In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.,* 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs,* pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099–6). Morpholinylethyl ester prodrugs may be prepared by reaction of the sodium salt of a compound of formula (I) (in a medium such as dimethylformamide) 4-(2-chloroethyl)morpholine hydrochloride (available from Aldrich Chemical Co., Milwaukee, Wis. USA, Item No. C4, 220–3).

(III) Method of Preparing the Benzo(b)thiophene-3-Glyoxylamide Compound (Starting Material for Preparing Other Compounds of the Invention)

The benzo(b)thiophene-3-glyoxylamide compounds are compounds of this invention and are also useful as intermediates or staring materials for preparing other compounds of the invention. The benzo(b)thiophene-3-glyoxylamide compounds are prepared by following a protocol such as Scheme 1 below:

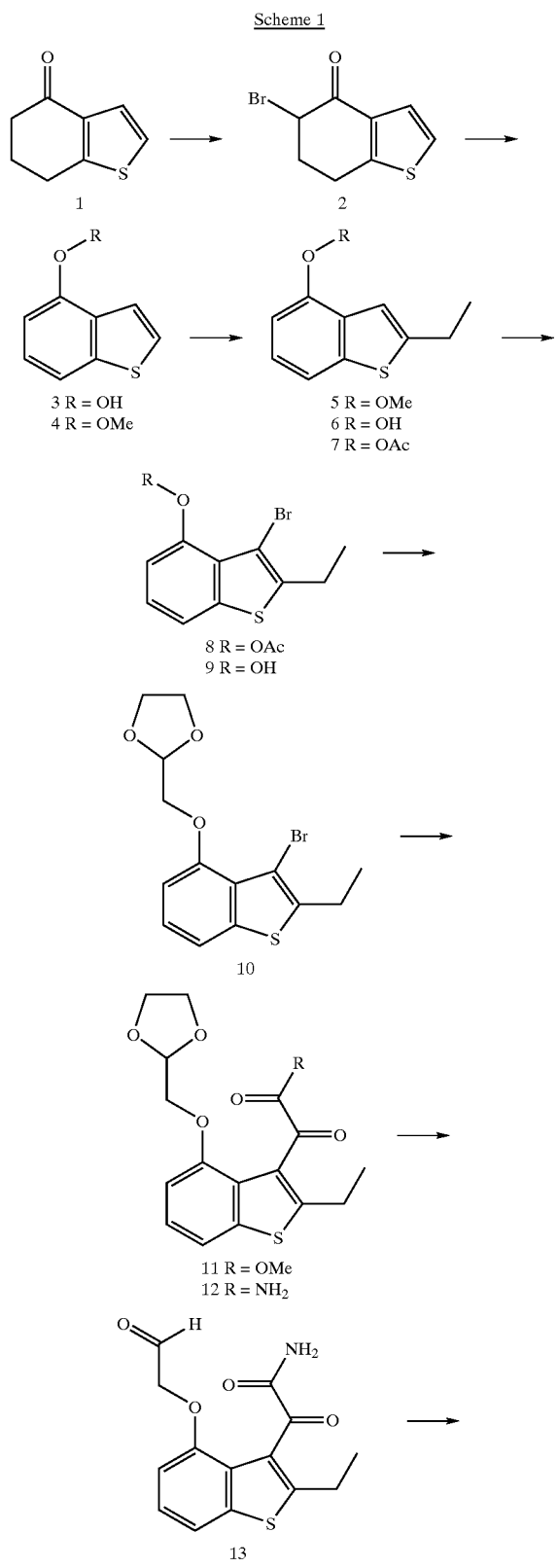

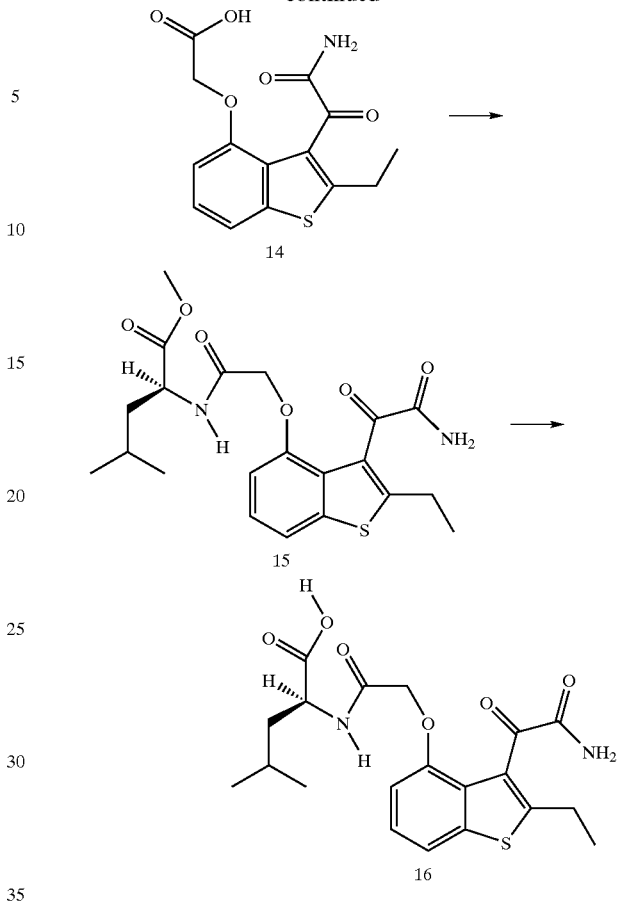

Synthesis of the starting material compounds useful for the present invention begins in one aspect with 6,7-dihydro-5H-benzo(b)thiophen-4-one compound of formula (1) or substituted derivatives thereof. The compound (1) is brominated with bromine in carbon tetrachloride at temperature ranging from about −30° C. to 30° C., over a period of from about 2 to 30 hours. (see Fleming, I. and Goldhill Jr., J. J. C. S Perkin I, 1493, (1980)). The product (2) is aromatized using sodium carbonate and lithium bromide to afford the benzo(b)thiophene alcohol of formula (3). The aromatization reaction requires heating in an anhydrous aprotic solvent such as for example, dimthylformamide. The product (3) may be isolated by aqueous work up. Procedures for aromatization of alicyclic ring compounds are known in the literature (see Advanced Organic Chemistry, J. March, Wiley interscience publishers, $3^{rd}$ edition, 1985, page 1052, and references therein).

The phenolic (OH group on benzo(b)thiophene) group may be protected for example, by alkylation. Other protecting groups i.e. organosilyl groups may also be used. To O-alkylated the benzo(b)thiophenol of formula (3), it is reacted with an alkyl halide, preferably alkyl iodide and more preferably methyl iodide using a base such as potassium carbonate in a solvent such as acetone. This results in a compound of formula (4) or analog thereof, depending on the protecting group. Substitution at the 2-position of the benzo(b)thiophene molecule may be effected by purchasing or preparing the starting material i.e. a compound (1) analog with that substitution already in place.

Alternatively substitution at the 2-position may be effected by generating a carbanion at the 2-position, which then reacts as a nucleophile with an electrophilic substrate. For example, the nucleophile generated by reacting a compound of formula (4) with an alkyllithium reagent, for example, n-BuLi or other organometallic agent may be reacted with an electrophile source such as for example alkyl halide or arylhalide. A particularly preferred alectrophile source for this step is ethyl iodide, ethylbromide or methyl iodide. The use of ethyl bromide for example, results in a compound of formula (5). One of skill in the art is aware that organolithium alkylation or arylation reactions are performed in anhydrous polar aprotic solvents such as for example tetrahydrofuran at temperatures ranging from about −80° C. to 20° C., preferably −80° C. to −10° C. followed by aqueous or non-aqueous work-up procedures. The hydroxy protecting group (for example, methyl in compound of formula 5) is removed by basic hydrolysis. First, the salt is prepared by reacting compound (5) with a sodium hydride dispersion (or other suitable base) in dimethylformamide at about 155° C. preferably in an oil bath. After about 2 hours or upon satisfactory completion of reaction (as tested by disappearance of diagnostic marker for methoxy starting material), the reaction mixture is cooled to about −30 to 20° C. Aqueous acid, preferably 5N HCl is added slowly while maintaining the temperature at below about 30° C. The resulting mixture is worked up under aqueous acidic conditions to afford the benzo(b)thiophenol compound of formula (6). The compound of formula (6) is re-protected, preferably with an electron withdrawing group for example the acetyl group. This affords protection of the —OH group at position 4 or 5 depending on the starting material used, and simultaneous activation of the 3-position by making the hydrogen atom at the 3-position more electron deficient. Acetylation is accomplished by reacting the compound of formula (6) with a base such as sodium hydroxide to form an alkoxide intermediate, followed by reaction with acetyl chloride for example, or other electron withdrawing protecting group, to form the compound of formula (7) or analog thereof. Having activated the 3-position on the benzo(b)thiophene ring from above, the acetylated benzothiophene compound (7) is halogenated, preferably brominated, at the 3-position by the use of n-bromosuccinimide or other appropriate halogenating agent. The bromination reaction involves stirring the mixture of reagents (compound 7, and n-bromosuccinimide) in a polar aprotic solvent from about 30 minutes to 20 hours. The reaction is typically complete in 1 to 4 hours. The resulting 3-bromo benzo(b)thiophene compound (8) may be isolated by chromatography or other known methods.

The acetyl protecting group as in compound (8), may be removed by treatment of a compound of formula (8) with an aqueous base solution. A preferred aqueous base solution is generated by addition of lithium hydroxide to a mixture of tetrahydrofuran, water and methanol. Other basic hydrolysis methods and reagents, are known to one of skill in the art. The incipient alkoxide (i.e. lithium alkoxide) may be isolated or converted to the free benzothiophenol by treatment with acid (e.g. HCl). The benzothiophenol compound of formula (9) or analog thereof, may be isolated by non-aqueous methods, i.e. by concentration of the product mixture followed by chromatography.

The benzo(b)thiophen-4-ol compound of formula (9) or analog thereof, is further elaborated or functionalized as desired, i.e. by forming an alkyl or aryl ether. A preferred protocol involves functionalization followed by protection or a simultaneous functionalization and protection as in the use of an acetal. For example, reaction of the compound of formula (9) with 2-bromomethyl-1,3-dioxolane and a base e.g. cesium carbonate, in an aprotic solvent results in the dioxolane compound of formula (10).

The compound of formula (10) from compound (9) serves to protect the incipient functionalized group at the 4 or 5-position (depending on the benzothiophene starting material) and allows for elaboration of the bromo or halo group at the 3-position. The halo group at the 3-position is then elaborated into desired functional groups. In particular, to prepare glyoxyl esters, a reagent such as dimethyloxalate is reacted with a carbanion generated by reaction of a compound of formula (10) with an alkyllithium e.g. n-butyllithium. The reaction of compound (10) with dimethyloxalate for example, affords a compound of formula (11).

The compound of formula (11) may be further elaborated to a compound of formula (12) for example, by reacting with excess ammonia, preferably under pressure. This may be accomplished by reacting compound (11) and ammonia in a pressure tube at about 30 to 80° C. for about 10 minutes to 4 hours, followed by appropriate cooling (i.e. about −78° C.) and isolation of product. Alternatively other methods of functionalizing the ester may be applied depending on substrate sensitivity. Other methods may include reagents for conversion of esters to amides (Larock, supra) i.e. the Weinreb amide procedure (supra) using substituted aluminoamide reagents, or conversion to activated esters followed by use of amide coupling agents.

With or without further modifications at the 3-position, compound (11) or (12) may be reacted with aqueous acid to remove the acetal protecting group and provide for example, the aldehyde of compound (13). The aldehyde (13) may be elaborated to the acid or other functional groups by methods known to one of skill in the art. For example, the aldehyde of formula 13 is converted to the free acid by oxidation. Various reagents are known in the art for aldehyde oxidations (see J. March, supra). One example is the use of sodium hypochlorite in t-butyl alcohol buffered with sodium dihydrogen phosphate, to oxidize the aldehyde (13) to the acid (14).

The acid compound of formula (14) may be converted to an ester i.e. the methyl ester, or to an acid salt i.e. the sodium salt by methods known to one of skill in the art. The acid (14), the acid salt, i.e. sodium salt, the ester, i.e. methyl ester, are compounds of the invention and are also useful as starting materials for other compounds of the invention.

For example, the compound of formula (14) may be converted to an amide or substituted amide, or acylamino acid derivative. Where a protected amino acid is used the resulting acylamino acid compound (e.g. compound 15) is also a compound of the present invention. Methods of preparing amides and derivatives thereof, or acylamino acid derivative compounds of the invention i.e. compounds of formula (15) or (16), are discussed herein and are generally known to one of skill in the art.

Preparing the Benzo(b)thiophene-3-glyoxylamide N-hydroxyfunctional amide Compounds The benzo(b)thiophene-3-glyoxylamide N-hydroxyfunctional amide compounds of the invention are prepared from the methyl ester compound 1A (scheme 2, below), or analogs thereof. The acid compound of formula (14) may be employed as starting material for the preparation of N-hydroxyfunctional amide compounds of the present invention by methods known to one of skill in the art. For example, in a protocol beginning with compound 14, the acid is converted to the N-hydroxyfunctional amide compound of formula (II") (See scheme 2 below)

Scheme 2

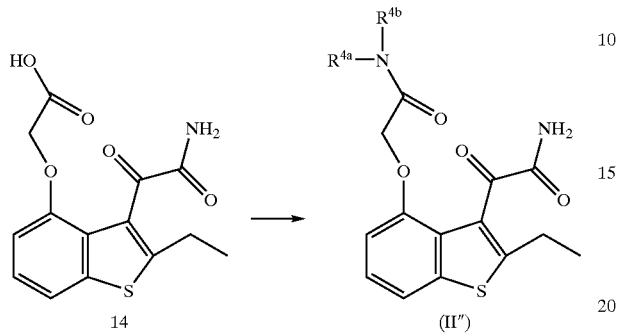

14 (II")

The above transformation may be accomplished by coupling the compound of formula 14 with a protected and/or substituted or unsubstituted hydroxylamine group or derivative, in the presence of a coupling agent. This results in a protected or unprotected N-hydroxyfunctional amide derivative of a compound of formula (II"). For example, the acid compound of formula (14) is reacted with o-(tert-butyldimethylsilyl) hydroxylamine at ambient temperature, in the presence of excess 2,4,6-collidine (collidine) and benzotriazol-1-yl-oxytris(dimethylamino)phosphonium hexafluorophosphonate (coupling catalyst, see *Tetrahedron Lett.*, 1219 (1975)) to form after about 1–10 hours, the o-(tert-butyldimethylsilyl) substituted N-hydroxyfunctional amide derivative. The silyl or other protecting group is removed by well known methods such as for example, the use of trifluoroacetic acid to afford the desired N-hydroxyfunctional amide compound of formula (II") wherein $R^{4a}$ is hydroxy and $R^{4b}$ is hydrogen.

Typically, the condensation or coupling is performed in a solvent such a dimethylformamide, tetrahydrofuran or aqueous mixtures of the like. In general, protic solvents are preferred for the purpose of this invention. The reaction is catalyzed by a base including weak organic or inorganic bases. Organic bases such as collidine are preferred. The reaction is also preferably run in the presence of agents that retard or reduce racemization of the hydroxyfunctional amide, the substituted hydroxylamine or its derivative. A particularly preferred agent for retarding racemeization where applicable, is benzotriazolyl-N-oxy-tris (dimethylamino)phosphonium hexafluorophosphate. Upon completion of the reaction, the mixture is concentrated in vacuo. The resulting product mixture is chromatographed or crystallized, e.g., by sonication to obtain the target compound.

An alternate preparation method is the inter-conversion of compounds of the invention as shown for example in Scheme (3):

Scheme 3

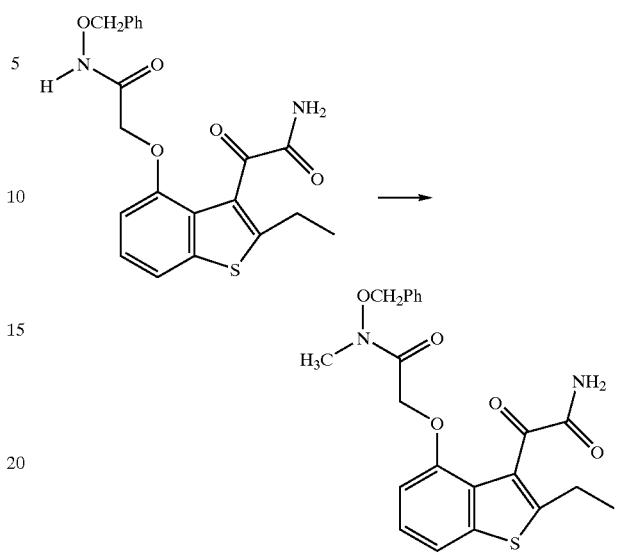

These and other methods are well known in the arts and can be found in reference texts such as for example J. March *Advanced Organic Chemistry,* Wiley Interscience publishers, New York, N.Y., 1985, and R. C. Larock *Comprehensive Organic Transformations,* VCH Publishers, New York, N.Y., 1989. The protected intermediates to compounds of formula (II) are useful $sPLA_2$ inhibitors and are also compounds of this invention.

The Benzo(b)thiophene-3-acetamide $sPLA_2$ Inhibitors

Benzo(b)thiophene-3-acetamide $sPLA_2$ inhibitors with the N-hydroxyfunctional amide, the acidic group or the acylamino acid group at the 4 or 5 position may be prepared from the dioxolane compound of formula (10) as shown below in scheme 4:

Scheme 4

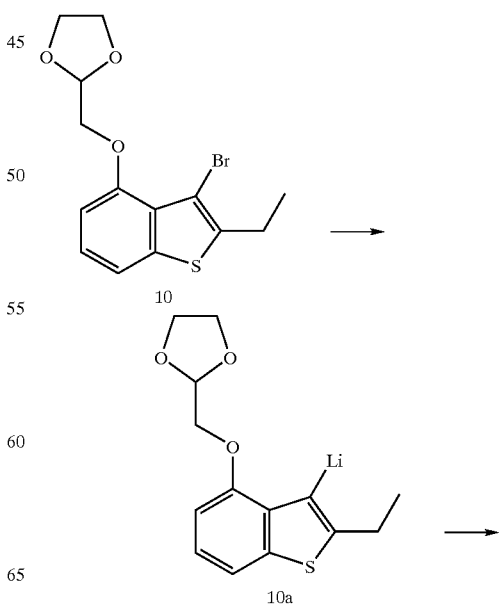

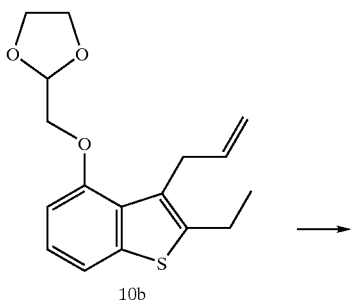

10b

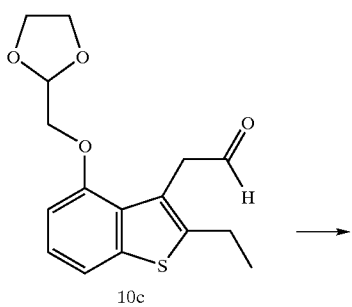

10c

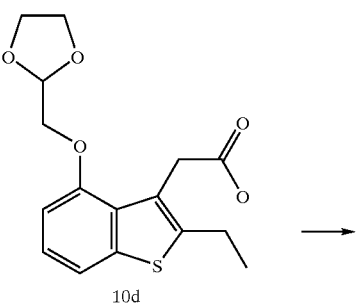

10d

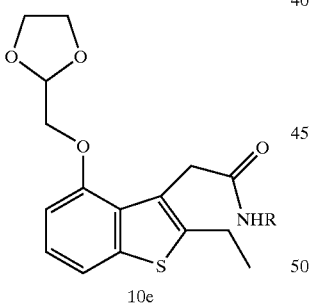

10e

For example, the compound of formula (10) may be metallated, preferably lithiated by a halogen metal exchange reaction in THF for example, at about −10° C. to about −70° C. using for example, n-butyllithium to form the un-isolated intermediate compound (10a). This is followed by addition of an allyl halide, preferably allyl iodide to form the terminal alkene compound (10b). Upon ozonolysis of the terminal alkene compound (10b) using ozonolysis procedures known to one of skillin the art, i.e., ozone in methylene chloride at about −78° C. to about −20° C., the aldehyde (10c) is obtained. The aldehyde (10c) is oxidized to the acid compound (10d) using for example, sodium hypochlorite in a suitable solvent, i.e a protic solvent such as aqueous tertiary butyl alcohol preferably buffered with sodium dihydrogen phopshare, to form the acid compound (10d). The acid (10d) is then amidated with ammonia in the presence of a coupling reagent e.g., BOP to form the acetamide compound (10e). Similarly other primary or secondary amines may be utilized in place of ammonia to afford the corresponding substituted acetamide compound.

The acetamide compound (10e) obtained from compound (10) as described above may be converted to the corresponding acidic group, N-hydroxyfunctional amide group, or acylamino acid group at the 4 or 5 position as described previously.

Alternatively, the acetamide compounds i.e., compound (10e) may be prepared by following a procedure according to Scheme 4a below:

Scheme 4a

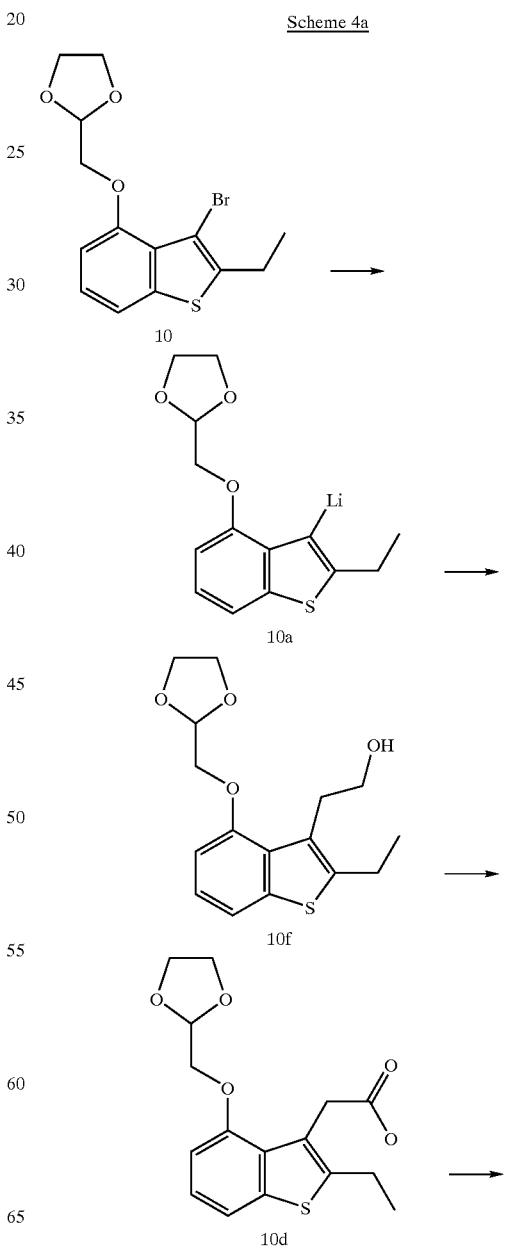

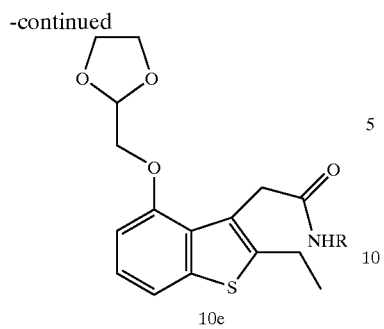

10e

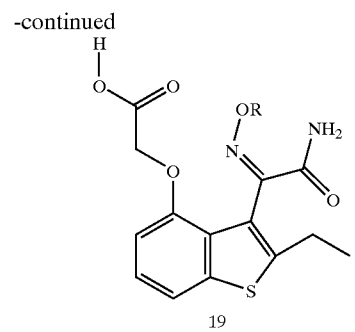

19

Compound (10d) may be prepared from compound (10) by halogen metal exchange at position 3 as described above to afford compound (10a). This is followed by a nucleophilic ring opening of an added epoxide, e.g. ethylene oxide. The resulting alcohol compound (10f) may be oxidized in one or two steps (directly or via the aldehyde) to the acid compound (10d). Methods for oxidation of alcohols to acids are well known to one of skill in the art, and are found in general reference texts (see Larock, infra). The acid compound (10d) is converted to the acetamide (10e) or a substituted acetamide as described previously.

Other methods of functionalizing the 3-position of compound (10), to an amide group may be found in R. C. Larock *Comprehensive Organic Transformations,* VCH Publishers, New York, N.Y., 1989.

The benzo(b)thiophene-3-acetamide compound prepared as discussed above is then elaborated to the N-hydroxyfunctional amide derivative by following a sequence of Scheme 1, 2 or 3 to elaborate the 4 or 5 position to the desired N-hydroxyfunctional amide, acylamino acid or acidic group compound as described previously.

Preparing the Benzo(b)thiophen-3-oxime Compounds

The benzo(b)thiophen-3-oxime compounds of the invention may be prepared following the protocol of scheme 5 below;

Scheme 5

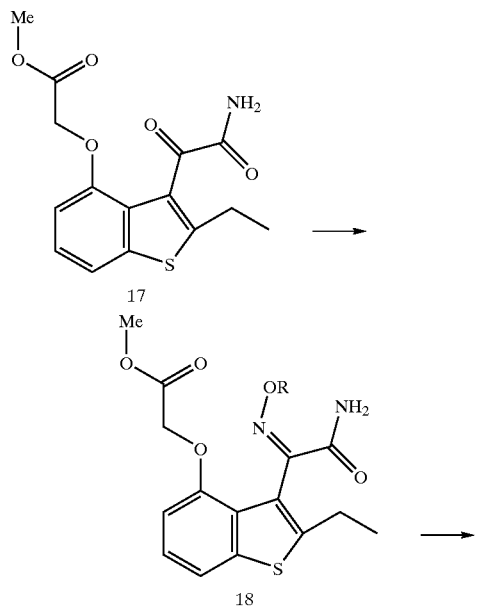

To introduce the oxime functionality, the methyl ester of the benzo(b)thiophene glyoxylamide compound (17) is heated with hydroxylamine hydrochloride (when R is H) in a THF/methanol mixture for about 1 to 8 hours or until the reaction is determined to be essentially complete. The reaction product is isolated by chromatography or other known laboratory procedure. Substituted oximes such as when R is methyl, ethyl, phenyl or other substituent may be prepared by reacting the corresponding substituted hydroxylamine hydrochloride or free base with the glyoxylamide as described supra. The ester functionality at the 4 or 5 position on the benzo(b)thiophene nucleus, as in for example, compound (18), may be converted to the acid by hydrolysis using lithium hydroxide or other known ester hydrolysis methods to afford compounds of formula (19). N-hydrofunctional-3-oxime amides and acylamino acid-3-oxime amides may be prepared by a protocol such as scheme (6) below.

Scheme 6

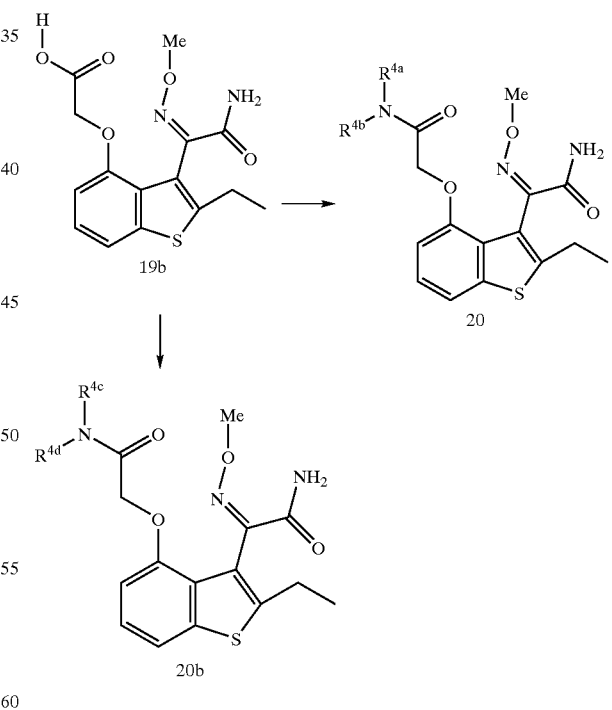

The oxime amide compound of formula (19b) for example, may be converted to a N-hydroxyfunctional amide functionality directly or via the acid functionality (e.g. Compound (19b), to afford for example the Compound of formula (20). Similarly, the oxime amide compound of formula (19b) may be converted to the acylamino acid compound of formula (20b)

General procedures for the conversion of organic acids to amino acid are well known to artisans in the field, and have been documented in general reference texts including, for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

The oxime amide compounds of scheme 6 such as the methyloxime compound (19b), can be converted to the corresponding acylamino acid or N-hydroxyfunctional amide derivative using the coupling reagent (BOP). The formation of the N-hydroxyfunctional amide derivative may be accomplished by coupling with various substituted or unsubstituted hydroxylamine compounds by general coupling procedures as described for the glyoxylamime compounds supra. Similarly, the acylamino acid derivative may be prepared by BOP catalyzed coupling of an N-terminus protected amino acid with an oxime amide compound such as compound (19b) having an acid group at the 4 or 5 position of the benzothiophene nucleus. Such methods are known to one skilled in the art. Additional references, or procedures are found in J. March *Advanced Organic Chemistry*, Wiley Interscience publishers, New York, N.Y., 1985; R. C. Larock *Comprehensive Organic Transformations*, VCH Publishers, New York, N.Y., 1989 and J. Jones *Amino Acids and Peptide Synthesis*, Oxford Science Publications, Stephen G. Davis, Editor, Oxford University Press Inc., New York, N.Y., 1992.

The Benzo(b)thiophene-3-glyoxylamide Acylamino Acid Derivatives

The benzo(b)thiophene-3-glyoxylamide acylamino acid derivative compounds of the invention are prepared by room temperature base catalyzed condensation of the amino acid protected at the acid terminus by a protecting group known in the literature (preferably as the methyl ester), with the benzo(b)thiophene-3-glyoxylamide acid derivative compound of formula (14) as shown in Scheme 7 below:

Scheme 7

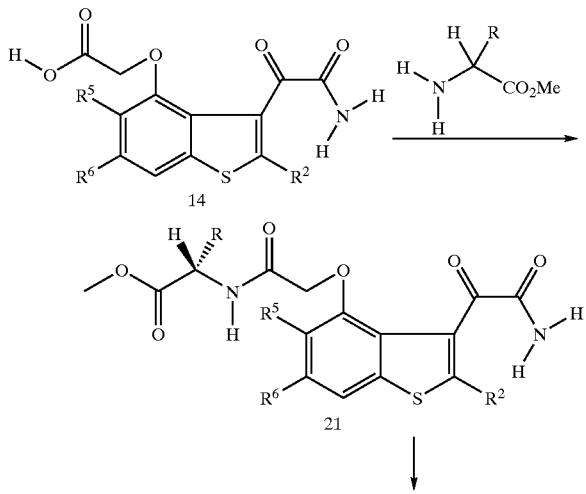

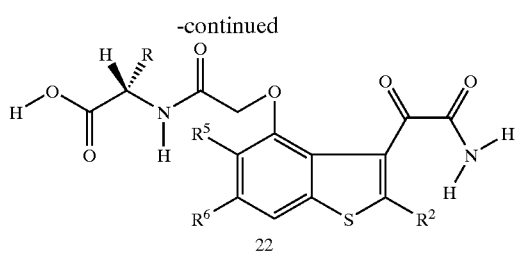

Typically, the condensation or coupling is performed in a solvent such as dimethylformamide, tetrahydrofuran or aqueous mixtures of the like. In general protic solvents are preferred for the purpose of this invention. The reaction is base catalyzed including weak organic or inorganic bases. Organic bases such as collidine are preferred. The reaction is also preferably run in the presence of agents that retard or reduce racemization of the amino acid or its derivative, such as for example, benzotriazolyl-N-oxy-tris(dimethylamino) phosphonium hexafluorophosphate(BOP). Upon completion of the reaction, the mixture is concentrated in vacuo. The resulting product mixture is chromatographed to obtain the target compound.

One of skill in the art is aware that the derivatives of the acid such as the acid salt or the methyl ester of the acid can be reacted with the amino acid or derivatives thereof to obtain the protected compound (21) or a corresponding derivative. Such methods are well known in the arts and can be found in reference texts such as for example J. March *Advanced Organic Chemistry*, Wiley Interscience publishers, New York, N.Y., 1985, and R. C. *Larock Comprehensive Organic Transformations*, VCH Publishers, New York, N.Y., 1989. The protected compound of formula (21) and analogs thereof, are also useful sPLA$_2$ inhibitors and are also compounds of this invention.

Benzo(b)thiophene-3-Oxime Amide Acylamino Acids, Benzo(b)thiophene-3-acetamide Acylamino acid Derivatives and Benzo(b)thiophene-3-amide Acylamino Acid Derivatives Acylamino acid derivatives of the benzo(b)thiophene oxime amides, benzo(b)thiophene amides, and benzo(b) thiophene-acetamides may be prepared from the corresponding acid such as the compound of formula (14) (scheme 1) by methods previously described for preparing the acylamino acid derivatives. For example the oxime amide of formula 19b (scheme 5), above may be converted to the corresponding acylamino acid derivative by an amide coupling reaction. Similarly, the benzo(b)thiophene-3-acetamide oxy acid compounds (acetamide derivatives of compound of formula (14), may be converted to the corresponding N-hydroxyfunctional amide or acylamino acid derivative at the 4-{ or 5-{position of the nucleus as described previously.

IV. Methods of Using the Compounds of the Invention

The benzo(b)thiophene compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with a therapeutically effective amount of benzo(b) thiophene compounds corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of the benzo(b)thiophene compound of the invention (see, formulae I and II).

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formula (I) or (II), or (II"), or (II') or (III) or (IIIb) or (IV) or (V) or (VI)) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the benzo(b)thiophene compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or (II) or (II') or (III) or (IIIb) or (IV) or (V) or (VI) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |

-continued

|                      | Quantity (mg/tablet) |
|----------------------|----------------------|
| Silicon dioxide, fumed | 10                 |
| Stearic acid         | 5                    |
| Total                | 665 mg               |

The components are blended and compressed to form tablets each weighing 665 mg

Formulation 3

An aerosol solution is prepared containing the following components:

|                                       | Weight |
|---------------------------------------|--------|
| Active ingredient                     | 0.25   |
| Ethanol                               | 25.75  |
| Propellant 22 (Chlorodifluoromethane) | 74.00  |
| Total                                 | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active ingredient                              | 60 mg   |
|------------------------------------------------|---------|
| Starch                                         | 45 mg   |
| Microcrystalline cellulose                     | 35 mg   |
| Polyvinylpyrrolidone (as 10% solution in water)| 4 mg    |
| Sodium carboxymethyl starch                    | 4.5 mg  |
| Magnesium stearate                             | 0.5 mg  |
| Talc                                           | 1 mg    |
| Total                                          | 150 mg  |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| Active ingredient          | 80 mg  |
|----------------------------|--------|
| Starch                     | 59 mg  |
| Microcrystalline cellulose | 59 mg  |
| Magnesium stearate         | 2 mg   |
| Total                      | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| Active ingredient              | 225 mg   |
|--------------------------------|----------|
| Saturated fatty acid glycerides| 2,000 mg |
| Total                          | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| Active ingredient             | 50 mg   |
|-------------------------------|---------|
| Sodium carboxymethyl cellulose| 50 mg   |
| Syrup                         | 1.25 ml |
| Benzoic acid solution         | 0.10 ml |
| Flavor                        | q.v.    |
| Color                         | q.v.    |
| Purified water to total       | 5 ml    |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg   |
|-------------------|----------|
| Isotonic saline   | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
REACTION BUFFER

| | |
|---|---|
| $CaCl_2 \cdot 2H_2O$ | (1.47 g/L) |
| KCl | (7.455 g/L) |
| Bovine Serum Albumin (fatty acid free) (Sigma A-7030, product of Sigma Chemical Co., St. Louis MO, USA) | (1 g/L) |
| TRIS HCl | (3.94 g/L) |
| pH | 7.5 (adjust with NaOH) |

ENZYME BUFFER—
  0.05 $NaOAc.3H_2O$, pH 4.5
  0.2 NaCl
  Adjust pH to 4.5 with acetic acid
DTNB—5,5'-dithiobis-2-nitrobenzoic acid
RACEMIC DIHEPTANOYL THIO—PC
  racemic 1,2-bis(heptanoylthio)-1,2-dideoxy-sn-glycero-3-phosphorylcholine
  TRITON X-100™ prepare at 6.249 mg/ml in reaction buffer to equal 10 uM.
REACTION MIXTURE—
A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

| Results | |
|---|---|
| Compound of Example # | $IC_{50}$ (uM) (micromolar) |
| 1 | 1.410 |
| 2 | 64.796 |
| 3 | 10.570 |

While the present invention has been illustrated above by certain specific embodiments, it is not intended that these specific examples should limit the scope of the invention as described in the appended claims.

EXPERIMENTAL

All of the products of the Examples described below as well as intermediates used in the following procedures showed satisfactory NMR and IR spectra. They also had the correct mass spectral values.

EXAMPLE 1

The preparation of (3-aminooxalyl-2-ethylbenzo[b]thiophen-4-yloxy)acetic acid

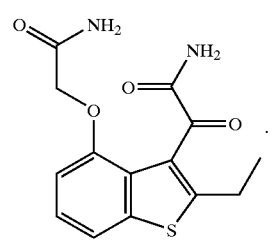

14

A. The preparation of benzo[b]thiophen-4-ol

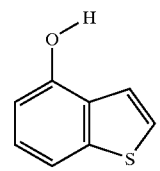

3

Bromine (3.38 mL, 65.7 mmol) dissolved in 40 mL carbontetrachloride was added dropwise over 1 h to a stirred solution of 6,7-dihydro-5H-benzo[b]thiophen-4-one, 1, (10.0 g, 65.7 mmol) dissolved in 500 mL $Et_2O$ at −13 to −7° C. After the addition was complete the reaction mixture was left in the −10° C. acetone bath. The bath was allowed to warm to ambient temperature and the reaction was stirred for 16 h. Distilled water (400 mL) was added to the reaction mixture. The organic layer was separated and washed with distilled water (200 mL) and brine (200 mL). The organic layer was concentrated to give 2 as a crude white solid. To the crude bromide, 2, in anhydrous DMF (140 mL) was added $Li_2CO_3$ (9.71 g, 131 mmol) and LiBr (11.41 g, 131 mmol). The mixture was heated to 110° C. for 20 min., then the reaction mixture was refluxed for 20 min. After cooling to near ambient temperature the reaction mixture was diluted with distilled water (250 ml) and EtOAc (400 mL). The mixture was poured into a separation funnel. The solids at the bottom were discarded without losing much of the aqueous layer. The organic layer was washed with 100 mL 0.1 N HCl, then brine (50 ml). To the aqueous layer was added 5 N HCl (26 mL) and EtOAc (200 mL). The organic layer was washed with distilled water (100 mL) and brine (50 mL). The organic layers were combined, dried over $Na_2SO_4$, filtered, concentrated, taken up in $CH_2Cl_2$ and chromatographed on silica (5% EtOAc in hexanes) to give 3 (6.45 g, 65%) as a white solid. $^1$H-NMR (CDCl$_3$) δ5.13 (s, 1H), 6.72 (d, J=7.8 Hz, 1H), 7.20 (t, J=7.8 Hz, 1H), 7.37 (d, J=5.9 Hz, 1H), 7.46–7.48 (m, 2H); ESIMS m/e 148.9 (M$^-$–1).

B. The Preparation of 4-methoxybenzo[b]thiophene

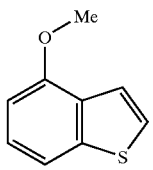

4

To 3 (3.27 g 21.8 mmol) in acetone (40 mL) at ambient temperature was added $K_2CO_3$ (3.61 g, 26.1 mmol) followed by methyliodide (2.71 mL, 43.5 mmol). After 2 h the reaction mixture was diluted with EtOAc (200 mL), then washed with distilled water (50 mL) and brine (50 mL). The organic layer was concentrated. The residue was taken up in $CH_2Cl_2$ and chromatographed on silica (2.5% EtOAc in hexanes) to give 4 (3.31 g, 93%) as a clear oil. $^1$H-NMR (CDCl$_3$) δ3.97 (s, 3H), 6.76 (d, J=7.8 Hz, 1H), 7.27 (t, J=7.8 Hz, 1H), 7.34 (d, J=6.3 Hz, 1H), 7.47 (d, J=7.8 Hz, 1H), 7.50 (d, J=6.3 Hz, 1H); FD m/e 164.1 (M$^+$).

C. The Preparation of 2-ethyl-4-methoxybenzo[b]thiophene

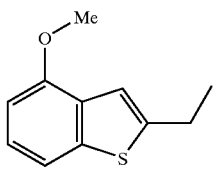

5

To 4 (0.357 g, 1.16 mmol) in anhydrous THF (4 mL) at −78° C. was added 1.6 M butyllithium in hexanes (0.80 mL, 1.28 mmol). After 30 minutes at −78° C. ethyliodide (2.44 mL, 30.4 mmol) was added. The cold bath was allowed to warm to −20° C. then 5 drops of distilled water were added and the reaction mixture was concentrated to half the volume. Hexanes (10 mL) were added, then the organic layer was separated and washed with distilled water (3 mL). The organic layer was dried over $Na_2SO_4$, filtered, concentrated and chromatographed on silica (100% hexanes) to give 5 as a clear oil (0.380 g, 97%) contaminated with a small amount of the starting material. $^1$H-NMR (CDCl$_3$) δ1.38 (t, J=7.8 Hz, 3H), 2.93 (q, J=7.8 Hz, 2H), 3.94 (s, 3H), 6.72 (d, J=7.8 Hz, 1H), 7.18 (s, 1H), 7.20 (dd, J=8.8, 7.8 Hz, 1H), 7.36 (d, J=8.8 Hz, 1H); ESIMS m/e 192.9 (M$^+$+1)

D. Preparation of 2-ethylbenzo[b]thiophen-4-ol

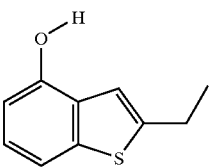

6

To 5 (3.25 g, 16.4 mmol) in anhydrous DMF (90 mL) at 0° C. was added ethanethiol (11.4 mL, 16.4 mmol). 60% wt. NaH oil dispersion (6.56 g, 16.4 mmol) was added in small portions. Then the reaction mixture was heated in a 155° C. oil bath for 2 h. After the flask was cooled it was placed in an ice bath. 5 N HCl (39.3 mL) was added slowly keeping the internal temperature below 30° C. The reaction mixture was diluted with Et$_2$O (500 mL), washed with distilled water (1×250 mL, and 4×100 mL) and washed with brine (100 mL). The organic layer was dried over $Na_2SO_4$, concentrated in vacuo at 30° C., and chromatographed on silica (1:1 $CH_2Cl_2$/hexanes, then 70% $CH_2Cl_2$ in hexanes) to give 6 (2.92 g, 100%) as a yellow oil. $^1$H-NMR (CDCl$_3$) δ1.25 (t, J=7.4 Hz, 3H), 2.83 (q, J=7.4 Hz, 2H), 6.64 (d, J=7.7 Hz, 1H), 7.03 (dd, J=7.9, 7.7 Hz, 1H), 7.12 (s, 1H), 7.23 (d, J=7.9 Hz, 1H), 9.76 (s, 1H); ESIMS m/e 177.1 (M$^-$–1).

E. The Preparation of Acetic Acid-2-ethylbenzo[b]thiophen-4-yl ester

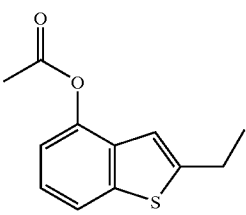

7

To 6 (0.507 g, 2.84 mmol) in THF (5 mL) at 0° C. was added NaH 60% wt. oil dispersion (0.125 g, 3.13 mmol). After stirring for 5 min., acetylchloride (0.214 mL, 3.13 mmol) was added dropwise, then the ice bath was removed. After 1 h the reaction mixture was diluted with Et$_2$O (25 mL), washed with distilled water (3×20 mL), concentrated and chromatographed on silica (0–50% $CH_2Cl_2$ in hexanes) to give 7 (0.6147 g, 98%) as a clear oil. $^1$H-NMR (CDCl$_3$) δ1.38 (t, J=7.5 Hz, 3H), 2.41 (s, 3H), 2.93 (q, J=7.5 Hz, 2H), 6.91 (s, 1H), 7.05 (d, J=7.7 Hz, 1H), 7.24 (dd, J=8.0, 7.7 Hz, 1H), 7.63 (d, J=8.0 Hz, 1H); FD m/e 220.1 (M$^+$).

F. The Preparation of Acetic Acid-3-bromo-2-ethylbenzo[b]thiophen-4-yl ester

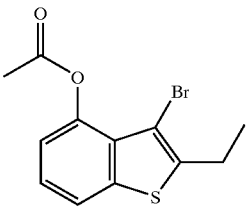

8

To 7 (0.470 g, 2.13 mmol) in THF (5 mL) at 0° C. was added N-bromosuccinimide (NBS) (0.417 g, 2.34 mmol). After stirring overnight at ambient temperature, the reaction mixture was concentrated to dryness. The residue was taken up in CH₂Cl₂ and chromatographed on silica (0–50% CH₂Cl₂ in hexanes) to give 8 (0.620 g, 97%) as a clear oil. ¹H-NMR (CDCl₃) δ1.33 (t, J=7.7 Hz, 3H), 2.43 (s, 3H), 2.93 (q, J=7.7 Hz, 2H), 7.03 (d, J=7.4 Hz, 1H), 7.13 (dd, J=8.0, 7.4 Hz, 1H), 7.66 (d, J=8.0 Hz, 1H); ESIMS m/e ⁷⁹Br 299.1 and ⁸¹Br 301.1 (M⁺+1).

G. The Preparation of 3-bromo-2-ethylbenzo[b]thiophen-4-ol

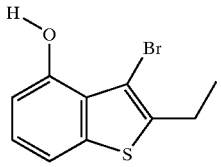

9

To 8 (0.501, 1.67 mmol) in a mixture of THF/MeOH/H₂O (3 mL/1.5 mL/0.5 mL) at ambient temperature was added 4.17 N LiOH (0.80 mL, 3.35 mmol). After 15 min. 5 N HCl (1.0 mL) was added dropwise, then the reaction mixture was concentrated in vacuo at 32° C. The residue was taken up in CH₂Cl₂, dried over Na₂SO₄, filtered, concentrated and chromatographed on silica (0–50% CH₂Cl₂ in hexanes) to give 9 (0.425 g, 99%) as a white solid. ¹H-NMR (CDCl₃) δ1.33 (t, J=7.8 Hz, 3H), 2.88 (q, J=7.8 Hz, 2H), 6.84 (d, J=8.8 Hz, 1H), 7.20 (t, J=8.8, Hz, 1H), 7.33 (d, J=8.8 Hz, 1H); ESIMS m/e ⁷⁹Br 257.0 and ⁸¹Br 259.0 (M⁺+1).

H. The Preparation of 2-[[(3-bromo-2-ethylbenzo[b]thiophen-4-yl)oxy]methyl]-[1,3]-dioxolane

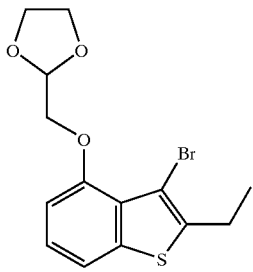

10

To 9 (1.03 g, 4.01 mmol) in anhydrous DMF (10 mL) at 0° C. was added 2-bromomethyl-1,3-dioxolane (2.49 mL, 24.0 mmol), followed by Cs₂CO₃ (4.57 g, 14.0 mmol). The ice bath was removed and the reaction was heated for 2 h at 55° C. After cooling to ambient temperature the reaction mixture was diluted with distilled water (60 mL), then extracted with EtOAc (150 mL). The organic layer was washed with distilled water (3×60 mL), then concentrated and chromatographed on silica (10–50% CH₂Cl₂ in hexanes) to give 10 contaminated with 2-bromomethyl-1,3-dioxolane. The 2-bromomethyl-1,3-dioxolane was removed by stirring the mixture in a 50° C. oil bath at reduced pressure (0.5 mmHg) for several hours to give 10 (1.06 g, 77%) as a colorless oil. ¹H-NMR (CDCl₃) δ1.30 (t, J=7.3 Hz, 3H), 2.91 (q, J=7.3 Hz, 2H), 3.95–4.10 (m, 4H), 4.13 (d, J=3.9 Hz, 2H), 5.47 (t, J=3.9 Hz, 1H), 6.77 (d, J=7.8 Hz, 1H), 7.20 (dd, J=8.3, 7.8 Hz, 1H), 7.36 (d, J=8.3 Hz, 1H); ESIMS m/e ⁷⁹Br 343.0 and ⁸¹Br 345.0 (M⁺+1).

I. The preparation of [4-[([1,3]-dioxolan-2-yl)methyloxy]-2-ethylbenzo[b]thiophen-3-yl]oxoacetic acid methyl ester

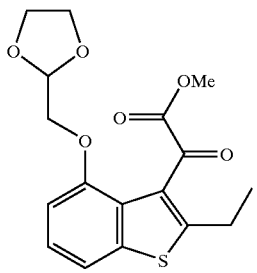

11

To 10 in THF (25 mL) at −78° C. was added 1.6 M BuLi in hexanes (1.75 mL, 2.80 mmol). After 8 min. the reaction mixture was cannula transferred to a flask containing dimethyloxalate (1.10 g, 9.32 mmol) in THF (25 mL) at −20° C. After 5 min. the cold bath was removed and the reaction warmed to ambient temperature. Saturated NH₄Cl solution (10 mL) was added followed by EtOAc (100 mL). The organic layer was separated and washed with distilled water (25 mL), then brine (25 mL). The organic layer was concentrated and chromatographed on silica (10–40% EtOAc in hexanes) to give 11 (0.380 g, 59%) as a yellow oil. ¹H-NMR (CDCl₃) δ1.35 (t, J=7.3 Hz, 3H), 2.96 (q, J=7.3 Hz, 2H), 3.87 (s, 3H), 3.89–4.00 (m, 4H), 4.10 (d, J=3.9 Hz, 2H), 5.21 (t, J=3.9 Hz, 1H), 6.84 (d, J=7.8 Hz, 1H), 7.25 (dd, J=8.3, 7.8 Hz, 1H), 7.40 (d, J=8.3 Hz, 1H); ESIMS m/e 350.9 (M⁺+1).

J. The Preparation of 2-[4-[([1,3]-dioxolan-2-yl)methyloxy]-2-ethylbenzo[b]thiophen-3-yl]-2-oxo-acetamide

12

To 11 (0.190 g, 0.542 mmol) in anhydrous THF (2 mL), cooled to −78° C. in a pressure bottle equipped with a septum and under N₂ atmosphere, was bubbled NH₃ gas. About 2 mL of NH₃ was trapped. The pressure bottle was sealed and heated to 55° C. for 1 h. The reaction vessel was allowed to cool to ambient temperature, then placed in a −78° C. bath to condense the ammonia. The cap was removed from the pressure bottle and the ammonia was allowed to evaporate. The reaction mixture was concentrated and chromatographed on silica (1:1 EtOAc/hexanes) to give 12 (0.168 g, 92%) as an off white solid. ¹H-NMR (CDCl₃) δ1.34 (t, J=7.3 Hz, 3H), 2.92 (q, J=7.3 Hz, 2H), 3.88–3.99 (m, 4H), 4.10 (d, J=4.2 Hz, 2H), 5.27 (t, J=4.2 Hz, 1H), 5.52 (br s, 1H), 6.80 (d, J=7.8 Hz, 1H), 6.90 (br s, 1H), 7.23 (dd, J=8.3, 7.8 Hz, 1H), 7.38 (d, J=8.3 Hz, 1H); ESIMS m/e 336.1 (M⁺+1).

K. The Preparation of [(3-aminooxalyl-2-ethylbenzo[b]thiophen-4-yl)oxy]acetic acid

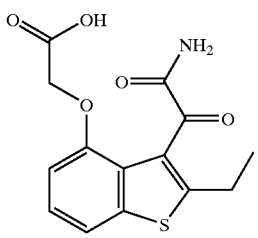

14

To 12 (0.146 g, 0.434 mmol) in anhydrous THF (3 mL) was added 5 N HCl (5 mL). After 1 h more 5 N HCl (4 mL) was added. After 45 min. the reaction mixture was diluted with 100 mL EtOAc and washed with distilled water (2×25 mL). The organic layer was dried over $Na_2SO_4$, filtered, concentrated in vacuo at 35° C. to give the crude aldehyde, 13, as a yellow solid. To the crude aldehyde, 13, in t-butanol (1.5 mL) and 2-methyl-2-butene (1.5 mL) was added a mixture of $NaClO_2$ (0.392 g, 4.34 mmol) and $NaH_2PO_4$ (0.599 g, 4.34 mmol) dissolved in distilled water (1.5 mL). The reaction was sluggish, so after 1.25 h 4 mL t-butanol, 2 mL distilled water and 2 mL THF were added. An additional 0.392 g $NaClO_2$ and 0.599 g $NaH_2PO_4$ dissolved in 2 mL distilled water were added and the reaction stirred vigorously for 17 h. The reaction mixture was diluted with EtOAc (35 mL) and the two layers were separated. The aqueous layer was washed with an additional 25 mL EtOAc. The combined organic layers were concentrated to about 2 mL and a yellow solid precipitate was filtered to give 14 (0.038 g). The filtrate was treated with THF/Hex/EtOAc to give more of 14 (0.036 g) as a yellow solid. Total: (0.074 g, 55%). $^1$H-NMR ($CD_3OD$) δ1.32 (t, J=7.8 Hz, 3H), 2.91 (q, J=7.8 Hz, 2H), 4.72 (s, 2H), 6.78 (d, J=7.8 Hz, 1H), 7.26 (dd, J=8.3, 7.8 Hz, 1H), 7.45 (d, J=8.3 Hz, 1H); ESIMS m/e 307.8 ($M^+$+1).

EXAMPLE 2

The Preparation of 2(S)-[2-[(3-aminooxalyl-2-ethylbenzo [b]thiophen-4-yl)oxy]acetylamino]-4-methylpentanoic cid methylester

15

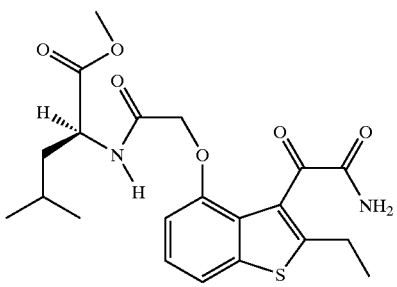

To 14 (0.0514 g, 0.167 mmol) in anhydrous DMF (0.5 mL) was added collidine (0.066 mL, 0.50 mmol), (S)-leucine methyl ester hydrochloride (0.0456 g, 0.251 mmol), and benztriazole-1-yloxy-tris(dimethylamino)phosphonium hexafluorophosphate (0.111 g, 0.251 mmol). After 2.5 h the reaction mixture was concentrated to dryness, taken up in $CH_2Cl_2$ and chromatographed on silica (0–20% EtOAc in $CH_2Cl_2$) to give 15 (0.057 g, 79%) as a yellow solid. $^1$H-NMR ($CDCl_3$) δ0.76 (d, J=6.8 Hz, 3H), 0.82 (d, J=6.8 Hz, 3H), 1.37 (t, J=7.3 Hz, 3H), 1.37 (m, 1H), 1.56–1.61 (m, 2H), 2.99 (q, J=7.3 Hz, 2H), 3.73 (s, 3H), 4.62–4.68 (m, 3H), 6.66 (d, J=7.8 Hz, 1H), 6.69 (s, 1H), 6.99 (s, 1H), 7.24 (dd, J=8.3, 7.8 Hz, 1H), 7.42 (d, J=8.3 Hz, 1H), 7.69 (br d, J=8.3 Hz, 1H); ESIMS m/e 435.2 ($M^+$+1).

EXAMPLE 3

The Preparation of 2(S)-[2-[(3-aminooxalyl-2-ethylbenzo [b]thiophen-4-yl)oxy]acetylamino]-4-methylpentanoic acid

16

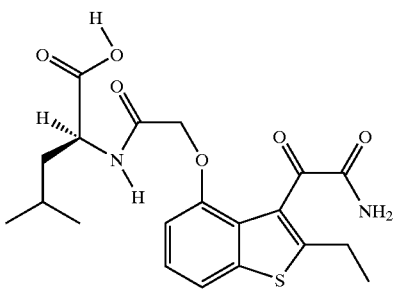

To 15 (0.0440 g, 0.101 mmol) in THF/MeOH (1 mL/0.33 mL) was added LiOH (0.0047 g, 0.11 mmol) dissolved in 0.17 mL distilled water. After 1 h 0.0023 g LiOH (s) dissolved in 0.1 mL distilled water was added and the reaction was heated to 50° C. for 1 h, then at ambient temperature for 16 h. 5 N HCl (0.034 mL, 0.17 mmol) was added and the reaction mixture was concentrated to near dryness, then diluted with distilled water (5 mL) and EtOAc (20 mL). The aqueous layer was washed with EtOAc (10 mL). The combined organic layers were concentrated to give a yellow residue which was dissolved in $CH_2Cl_2$ (2 mL) and hexanes (2 mL), then slowly concentrated in vacuo at 30° C. to give 16 (0.0385 g, 91%) as a yellow solid. $^1$H-NMR ($CDCl_3$) δ0.73 (d, J=6.4 Hz, 3H), 0.78 (d, J=6.8 Hz, 3H), 1.28–1.32 (m, 1H), 1.37 (t, J=7.3 Hz, 3H), 1.51–1.67 (m, 2H), 2.96 (q, J=7.3 Hz, 2H), 4.56–4.62 (m, 1H), 4.68 (s, 2H), 6.66 (d, J=7.8 Hz, 1H), 7.00 (s, 1H), 7.12 (s, 1H), 7.23 (dd, J=8.3, 7.8 Hz, 1H), 7.43 (d, J=7.8 Hz, 1H), 7.46 (d, J=8.3 Hz, 1H); ESIMS m/e 420.9 ($M^+$+1).

We claim:

1. A benzo(b)thiophene compound represented by the formula (I), or a pharmaceutically acceptable salt or solvate thereof;

(I)

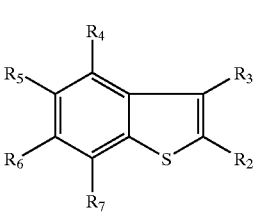

wherein;

$R_2$ is hydrogen, or a group containing 1 to 4 non-hydrogen atoms plus any required hydrogen atoms;

$R_3$ is —($L_3$)—Z, where —($L_3$)— is a divalent linker group selected from a bond or a divalent group selected from:

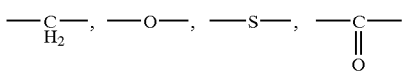

and Z is selected from a group represented by the formulae,

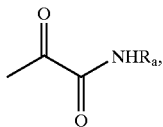

$R_4$ is the group —(Lc)-acylamino acid group), wherein —(Lc)—, is an acylamino acid linker having an acylamino acid linker length of 1 to 8;
$R_5$ is selected from hydrogen,
$R_6$ and $R_7$ are selected from hydrogen.

2. The compound of claim 1 wherein $R_2$ is hydrogen, $C_1$–$C_4$ alkyl, $C_2$–$C_4$ alkenyl, —O—($C_1$–$C_3$ alkyl), —S—($C_1$–$C_3$ alkyl), $C_3$–$C_4$ cycloalkyl, —$CF_3$, halo, —$NO_2$, —CN, or —$SO_3$.

3. The compound of claim 2 wherein the acylamino acid linker —($L_c$)—, for $R_4$ is a divalent group independently selected from,

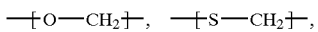

4. The compound of claim 1 wherein $R_4$ is the group, —($L_c$)-(acylamino acid group) and wherein the (acylamino acid group) is:

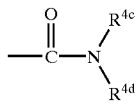

and $R^{4c}$ is selected from the group consisting of H, ($C_1$–$C_6$) alkyl, ($C_1$–$C_6$)alkoxy, heteroaryl and aryl; and wherein $NR^{4d}$ is an amino acid residue with the nitrogen atom being part of the amino group of the amino acid.

5. A method for treatment of a human afflicted with Inflammatory Diseases, said method comprising administering to said human in need of such treatment, a therapeutically effective amount of compound according to claim 1 or a pharmaceutically acceptable salt or solvate thereof selected from the group consisting of: (phenylmethyloxy)acetamide;
N-[2-[[3-(Aminooxoacetyl)-2-ethylbenzo(b)thiophen-4-yl]oxy]acetyl]glycine;
N-[2-[[3-(Aminooxoacetyl)-2-ethylbenzo(b)thiophen-4-yl]oxy]acetyl]glycine methyl ester;
N-[2-[[3-(Aminooxoacetyl)-2-ethylbenzo(b)thiophen-4-yl]oxy]acetyl]-L-alanine;
N-[2-[[3-(Aminooxoacetyl)-2-ethylbenzo(b)thiophen-4-yl]oxy]acetyl]-L-alanine methyl ester;
N-[2-[[3-(Aminooxoacetyl)-2-ethylbenzo(b)thiophen-4-yl]oxy]acetyl]-L-leucine;
N-[2-[[3-(Aminooxoacetyl)-2-ethylbenzo(b)thiophen-4-yl]oxy]acetyl]-L-leucine methyl ester;
N-[2-[[3-(Aminooxoacetyl)-2-ethylbenzo(b)thiophen-4-yl]oxy]acetyl]-L-aspartic acid;
N-[2-[[3-(Aminooxoacetyl)-2-ethylbenzo(b)thiophen-4-yl]oxy]acetyl]-L-aspartic acid dimethyl ester;
N-[2-[[3-(Aminooxoacetyl)-2-ethylbenzo(b)thiophen-4-yl]oxy]acetyl]-L-phenylalanine;
N-[2-[[3-(Aminooxoacetyl)-2-ethylbenzo(b)thiophen-4-yl]oxy]acetyl]-L-phenylalanine methyl ester;
[2-[[3-(Aminooxoacetyl)-2-ethylbenzo(b)thiophen-4-yl]oxy]acetamido]malonic acid;
[2-[[3-(Aminooxoacetyl)-2-ethylbenzo(b)thiophen-4-yl]oxy]acetamido]malonic acid dimethyl ester
N-[2-[[3-(Aminooxoacetyl)-2-ethylbenzo(b)thiophen-4-yl]oxy]acetyl]-L-valine;
N-[2-[[3-(Aminooxoacetyl)-2-ethylbenzo(b)thiophen-4-yl]oxyl]acetyl]-L-valine methyl ester;
N-[2-[[3-(Aminooxoacetyl)-2-ethylbenzo(b)thiophen-4-yl]oxy]acetyl]-L-isoleucine; and
N-[2-[[3-(Aminooxoacetyl)-2-ethylbenzo(b)thiophen-4-yl]oxy]acetyl]-L-isoleucine methyl ester.

6. A benzo(b)thiophene compound represented by the formulae (C17) or (C18);

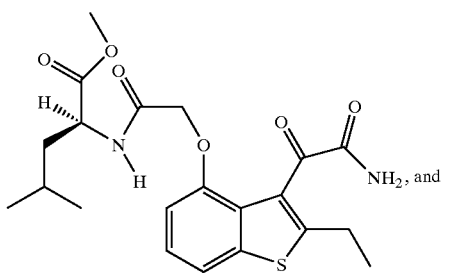

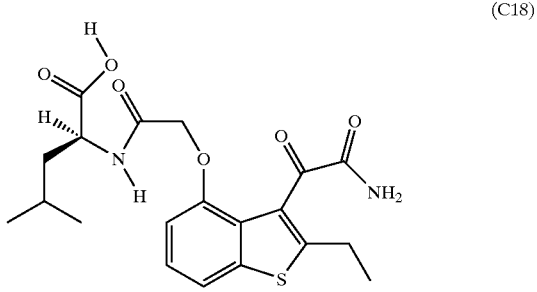

or pharmaceutically acceptable salts thereof.

7. A pharmaceutical formulation comprising a benzo(b)thiophene compound as claimed in claim 1 together with a pharmaceutically acceptable carrier or diluent therefor.

8. A method of treating a mammal to alleviate the pathological effects of Inflammatory Diseases; wherein the method comprises administering to said mammal a therapeutically effective amount of a benzo(b)thiophene compound as claimed in claim 1.

* * * * *